(12) United States Patent
Imai et al.

(10) Patent No.: US 12,011,385 B2
(45) Date of Patent: Jun. 18, 2024

(54) COLLECTING IMPLEMENT

(71) Applicant: INTRON SPACE INC., Tokyo (JP)

(72) Inventors: Shigeo Imai, Tokyo (JP); Takashi Kondo, Tokyo (JP)

(73) Assignee: INTRON SPACE INC., Tokyo (JP)

( * ) Notice: Subject to any disclaimer, the term of this patent is extended or adjusted under 35 U.S.C. 154(b) by 0 days.

(21) Appl. No.: 18/261,626

(22) PCT Filed: Jul. 27, 2022

(86) PCT No.: PCT/JP2022/028923
§ 371 (c)(1),
(2) Date: Jul. 14, 2023

(87) PCT Pub. No.: WO2023/013492
PCT Pub. Date: Feb. 9, 2023

(65) Prior Publication Data
US 2024/0033119 A1 Feb. 1, 2024

(30) Foreign Application Priority Data
Jul. 31, 2021 (JP) .................................. 2021-126340

(51) Int. Cl.
*A61F 5/451* (2006.01)
(52) U.S. Cl.
CPC .................................. *A61F 5/451* (2013.01)
(58) Field of Classification Search
CPC .. A61F 5/4404–443; A61F 5/453; A61F 2/04; A61M 1/76; A61M 1/84–87;
(Continued)

(56) References Cited

U.S. PATENT DOCUMENTS 4,581,026 A * 4/1986 Schneider ............. A61L 24/043
604/352
5,458,114 A 10/1995 Herr
(Continued)

FOREIGN PATENT DOCUMENTS

CN 103717180 A 4/2014
JP H 0581445 4/1993
(Continued)

OTHER PUBLICATIONS

Japanese Decision to Grant a Patent (w/ English translation) for corresponding Japanese Application No. 2022-562252, dated Jul. 6, 2020, 5 pages.
(Continued)

*Primary Examiner* — Susan S Su
(74) *Attorney, Agent, or Firm* — Dority & Manning, P.A.

(57) ABSTRACT

A collecting implement includes a cylindrical body portion having a stretchability; and a hollow portion formed in the body portion, wherein the hollow portion includes an inlet portion which is formed such that one end side of the body portion is open and through which a material is introduced; and a collecting portion which is formed continuously from the inlet portion and contains the material. In the collecting portion, a predetermined part is more stretchable than a part of the collecting portion other than the predetermined part so that the predetermined part can bulge toward an outer side of the body portion when the material introduced from the inlet portion is contained.

8 Claims, 20 Drawing Sheets

(58) Field of Classification Search
CPC .............. A61M 25/00; A61M 25/0017; A61M 25/0051; A61M 25/0054; A61M 25/0074–0075; A61M 2025/0076–0078; A61M 27/00–008; A61M 2027/004; A61M 2025/0024

See application file for complete search history.

(56) References Cited

U.S. PATENT DOCUMENTS

| | | | | |
|---|---|---|---|---|
| 5,618,277 | A | * | 4/1997 | Goulter .................. A61F 5/453 604/350 |
| 6,007,521 | A | * | 12/1999 | Bidwell .................. A61F 5/453 604/99.04 |
| 6,527,755 | B1 | * | 3/2003 | Salama ................ A61F 2/0013 604/326 |
| 2005/0251100 | A1 | | 11/2005 | Charles |

FOREIGN PATENT DOCUMENTS

| | | |
|---|---|---|
| JP | 3146490 U | 12/2008 |
| JP | 2013-099502 A | 5/2013 |
| JP | 2013-163043 A | 8/2013 |
| JP | 2016-052393 A | 4/2016 |
| JP | 2017123999 A | 7/2017 |

OTHER PUBLICATIONS

Japanese Office Action (w/ English translation) for corresponding Japanese Application No. 2022-562252, dated Feb. 17, 2023, 4 pages.

International Search Report (with English translation) for Application No. PCT/JP2022/028923, dated Sep. 20, 2022, 4 pages.

English translation of the Chinese Office Action for corresponding Application No. 202280012374.8, issued Feb. 8, 2024, 6 pages.

* cited by examiner

COLLECTING IMPLEMENT

CROSS REFERENCE TO RELATED APPLICATIONS

This application is the U.S. National Stage entry of International Application No. PCT/JP2022/028923, filed on Jul. 27, 2022, which, in turn, claims priority to Japanese Patent Application No. 2021-126340, filed on Jul. 31, 2021, both of which are hereby incorporated herein by reference in their entireties for all purposes.

TECHNICAL FIELD

The present invention relates to a collecting implement, particularly to a collecting implement comprising a cylindrical body portion having a softness and a stretchability and a hollow portion formed in the body portion.

BACKGROUND ART

Collecting implements for collecting and containing a liquid, gel-like, or semi-solid material have been used widely and used for various purposes, for example, for collecting the waste discharged from the human body or a variety of structures, the harvest gathered from the natural environment, or the like.

Patent Literature 1 discloses a collecting implement comprising a collecting bag for collecting the excrement and a catheter tube which is connected to the collecting bag to introduce the excrement into the collecting bag, in which the collecting bag and the catheter tube are treated with deodorizing measures. Further, Patent Literature 2 discloses a collecting implement comprising an underwear-like clothing body sewn using a stretchable fiber material (for example, cotton) with an opening provided at a part covering the vulva of a woman and a urine collecting bag attached to the clothing body. Moreover, Patent Literature 2 discloses an embodiment in which the urine collecting bag is provided with a check valve member. Further, Patent Literature 3 discloses a collecting implement comprising an elongated urine collecting bag having a penis receiving opening for receiving the penis of the user at a proximal end portion, a ring-shaped seal member attached on the outer peripheral surface of the urine collecting bag around the penis, and a fixing ring. Moreover, Patent Literature 3 discloses that a head part of the urine collecting bag is folded back and a clip for closing the folded head part from the outer side is provided.

PRIOR ART DOCUMENT

Patent Literature

Patent Literature 1: JP2013-163043A
Patent Literature 2: JP2016-52393A
Patent Literature 3: JP2013-99502A

SUMMARY OF INVENTION

Technical Problem

In the above types of collecting implements, when a portion for collecting and containing a material and a portion for introducing the material into this container portion are made from separate members and these members are connected to each other to form a collecting implement, it is feared that there may occur a leakage of the material from such a connection part.

On the other hand, in view of prevention of a leakage of a material from a connection part or the like, it is typically supposed to employ a hard member material for the connection part of each member, whereas, when a collecting implement is to be attached to the human body, it is also feared that the hardness of a member material employed for the connection part may cause comfortability, mobility, and the like for the user to decrease.

Further, when a collecting implement is not to be attached to the human body but is to be used for the purpose of, for example, collecting the waste from a pipe, it is also feared that the hardness of a connection part may lower the attachment property and thus make it difficult to attach the collecting implement.

The present invention has been made in view of the above circumstances and it is an object of the present invention to provide a collecting implement capable of preventing a leakage of a collected material and generating a good feeling during use.

Solution to Problem

A collecting implement according to the present invention to achieve the above object comprises: a cylindrical body portion having a softness and a stretchability; and a hollow portion formed in the body portion, wherein the hollow portion comprises: an inlet portion which is formed such that one end side of the body portion is open and through which a material is introduced; and a collecting portion which is formed continuously from the inlet portion and contains the material, and in the collecting portion, a predetermined part is more stretchable than a part of the collecting portion other than the predetermined part so that the predetermined part can bulge toward an outer side of the body portion when the material introduced from the inlet portion is contained.

Accordingly, the inlet portion into which the material is introduced and the collecting portion which contains the material are formed integrally as the hollow portion in a seamless manner in the body portion, thereby restraining the material introduced or contained from leaking out.

Further, the body portion having the hollow portion in which the inlet portion and the collecting portion are integrally formed in a seamless manner is formed in a cylindrical shape to have a softness and a stretchability while a hard part does not interpose, and accordingly a good feeling during use is achieved.

The collecting portion of the collecting implement is formed to be displaced from a center axis of the body portion in such a manner as to be partially thin in relation to the body portion, and the body portion is provided with an index for indicating a thin portion at the body portion.

Further, the collecting implement is configured such that a check valve for preventing the material contained in the collecting portion from flowing back to the inlet portion side is disposed between the collecting portion and the inlet portion.

The hollow portion of the collecting implement comprises: an outlet portion which is formed to be thick in relation to the collecting portion and communicates with an opening at the other end side of the body portion, and through which the material is discharged; and a discharge mechanism which applies a force acting on the collecting portion in which the material is contained so as to discharge the material through the outlet portion.

The collecting implement may be configured such that the body portion on the other end side is bent toward the one end side, thereby preventing the material from being discharged through the outlet portion, or may be configured such that a fitting portion which can fit the body portion to an excretory part of the human body is formed integrally with the body portion on the inlet portion side.

The collecting implement according to the present invention to achieve the above object comprises: a cylindrical body portion having a softness and a stretchability; and a hollow portion formed in the body portion, wherein the hollow portion comprises: an inlet portion which is formed such that one end side of the body portion is open and through which a material is introduced; and a collecting portion formed continuously from the inlet portion in which the body portion is formed to be thin in relation to the inlet portion, the collecting portion thus having a protrusion part which protrudes from the body portion, and the protrusion part bulges toward an outer side of the protrusion part when the material is contained.

The collecting implement according to the present invention to achieve the above object comprises: a cylindrical body portion having a softness and a stretchability; an inlet portion which is formed such that one end side of the body portion is open and through which a material is introduced; a collecting portion formed continuously from the inlet portion in which the body portion is formed to be thin in relation to the inlet portion so that a part formed to be thin of the body portion bulges toward the outer side of the body portion when the material introduced from the inlet portion is contained in the collecting portion; and an attachment portion which comprises: a fitting portion which is fitted to the penis and covers the external urethral orifice; and a check valve which is formed integrally with the fitting portion and prevents the material contained in the collecting portion from flowing back to the inlet portion side, the attachment portion tightly fitting to the body portion at the inlet portion.

Effect of Invention

According to this invention, a leakage of a collected material can be restrained and a good feeling during use is achieved

DESCRIPTION OF EMBODIMENTS

In the following, a collecting implement according to embodiments of the present invention will be described with reference to FIG. 1 to FIG. 26.

First Embodiment

First, a collecting implement according to a first embodiment will be described with reference to FIG. 1 to FIG. 8.

Figure 1:
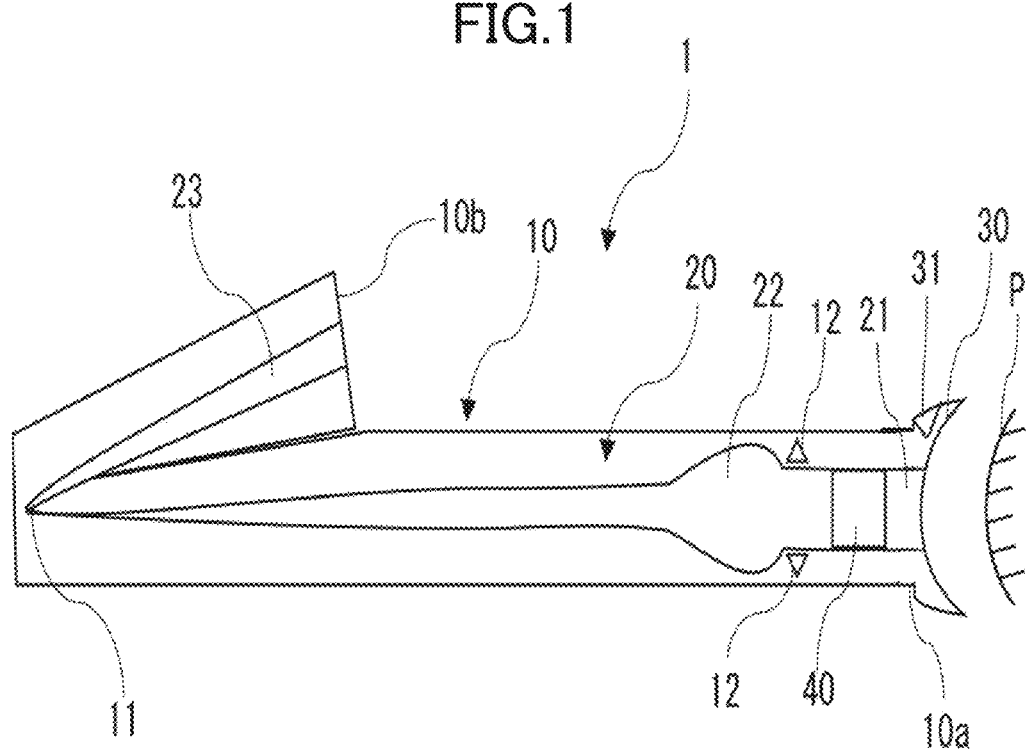
FIG. 1 is a schematic diagram generally illustrating a collecting implement according to a first embodiment of the present invention.

FIG. 1 is a schematic diagram generally illustrating a collecting implement according to the present embodiment. As illustrated, a collecting implement 1 comprises as main components a body portion 10, a hollow portion 20 formed in the body portion 10, and a fitting portion 30 formed with the body portion 10.

In the present embodiment, the body portion 10 is made of an elastomer having a softness in which the hardness is extra low (less than or equal to 20°) on the basis of a durometer type E (Shore E) (or E type durometer) in accordance with "JIS K 6253" in such a manner as to be sufficiently lower than the skin hardness as well as a stretchability in which the elongation percentage is more than or equal to approximately 70%. Note that, in consideration of comfortability, the body portion 10 is preferably softer than the skin hardness. The skin hardness is approximately around 20°. Note that the hardness of the inner side of the arm or leg is approximately 10° to 15°. Thus, the body portion 10 preferably has a hardness less than or equal to 20°, more preferably less than or equal to 10°.

Moreover, the elongation percentage at which the skin has a high stretchability and stretches to the greatest extent is generally approximately 70%. Accordingly, the stretchability of the body portion 10 is preferably at least 70% or more. Preferably, the stretchability of the body portion 10 is more than or equal to 100%, more preferably between 2,000% and 3,000%. Note that using an elastomer, a stretchability between 2,000% and 3,000% can be achieved.

In the present embodiment, the body portion 10 has a long cylindrical shape having one end 10a and the other end 10b, in which the body portion 10 has a bent portion 11 formed by bending, at an optional position in the long direction, the body portion 10 on the other end 10b side toward the one end 10a side, and has a hollow portion 20 which communicates the one end 10a side and the other end 10b side with each other.

In the present embodiment, the body portion 10 is provided with an index 12 for indicating a thin portion at a partially thin part (predetermined part) of the body portion 10 which corresponds to the position at which a collecting portion 22 as described below constituting the hollow portion 20 is provided.

In the present embodiment, the hollow portion 20 includes an inlet portion 21 which is formed such that the one end 10a side is open, the collecting portion 22 which is formed continuously from the inlet portion 21 and an outlet portion 23 which is formed continuously from the collecting portion 22.

The inlet portion 21 is an introduction passage through which a material is introduced from an opening having a circular shape at the one end 10a side, and is formed to be comparatively thick in relation to the body portion 10. The circular shape of the one end 10a side may be replaced by an elliptical shape, a polygonal shape, or the like.

In the present embodiment, the collecting portion 22 is formed to have a larger diameter than the inlet portion 21 and is a material reservoir portion for containing the material introduced from the inlet portion 21. In the collecting portion 22, the predetermined part is more stretchable than the part of the collecting portion 22 other than the predetermined part. In this case, it is considered that the predetermined part is thin so as to be more stretchable than the part other than the predetermined part. In addition, the predetermined part can bulge toward the outer side of the body portion 10 when the material introduced from the inlet portion 21 is contained in the collecting portion 22. Note that the predetermined part may be softer than the part of the collecting portion 22 other than the predetermined part.

Figure 2:
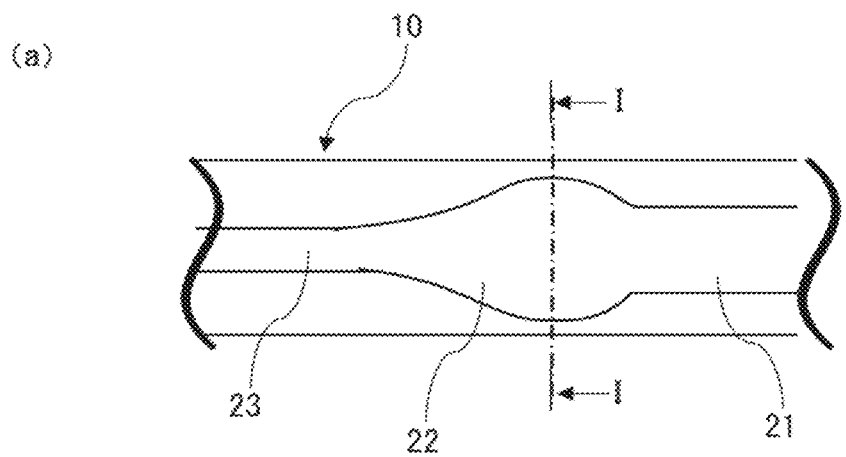
FIG. 2 is similarly a schematic diagram generally illustrating a configuration of a collecting portion of the collecting implement according to this embodiment.
Figure 2:
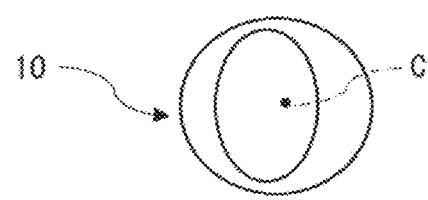
Figure 3:
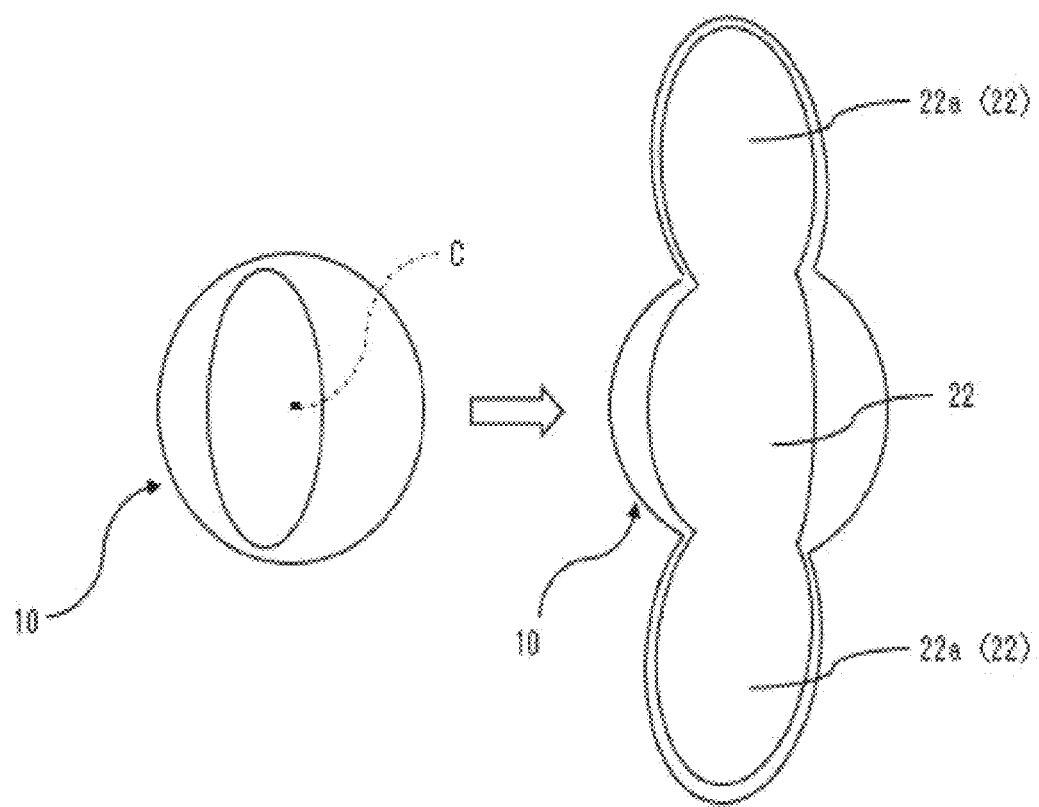
FIG. 3 is similarly a schematic diagram generally illustrating a configuration of the collecting portion of the collecting implement according to this embodiment.

FIG. 2 and FIG. 3 are each a schematic diagram generally illustrating a configuration of the collecting portion 22. As illustrated in FIG. 2(a), in the collecting portion 22, a part or the entirety of the body portion 10 corresponding to the position at which the collecting portion 22 is disposed is formed to be thin in relation to the inlet portion 21. A part which is formed at this thin film is the predetermined part. The predetermined part which is formed at this thin film is more stretchable than the part thicker than the predetermined part other than the predetermined part. Note that in an illustrative embodiment other than the embodiment in which the collecting portion 22 is formed to have a larger diameter than the inlet portion 21, the collecting portion 22 may be formed to be thin such that the outer diameter is reduced while the inner diameter remains the same.

FIG. 2(b) is a schematic sectional view along line I-I of FIG. 2(a). As illustrated in FIG. 2(b), in the present embodiment, the collecting portion 22 is formed to be displaced from a center axis C of the body portion "To be displaced from the center axis C of the body portion 10" means that an inner wall positioned around the center axis C of the body portion 10 is not disposed equidistant from the center axis C. Thereby, the body portion 10 is formed such that a part corresponding to the position at which the collecting portion 22 is disposed is partially thin.

Since, the body portion 10 has a softness in which the hardness is extra low and a high stretchability, as illustrated in FIG. 3, the thin part of the body portion bulges toward the outer side of the body portion 10 so that a bulge portion 22a is formed when the material introduced from the inlet portion 21 is contained in the collecting portion 22. The collecting portion 22 may have a contact surface which comes into contact with the human body during use. In this case, the bulge portion 22a (the entirety or a part of the predetermined part) may be arranged at a different position than the contact surface for the human body. Such an arrangement of the bulge portion 22a allows the human body to avoid being pressed while the bulge portion 22a bulges so that discomfort can be avoided.

Thus, the collecting portion 22 bulges toward the outer side of the body portion 10 so that the bulge portion 22a is formed, thereby securing an area for containing the material introduced from the inlet portion 21.

In the present embodiment, the collecting portion 22 is formed to be displaced from the center axis C of the body portion 10, thereby optionally defining the partially thin part of the body portion 10. Accordingly, the part at which the collecting portion 22 bulges toward the outer side of the body portion 10 is controlled.

As illustrated in FIG. 1, in the present embodiment, the outlet portion 23 is a discharge passage which is formed to be sufficiently thick in relation to the collecting portion 22 and communicates with a circular opening at the other end 10b side, and through which the material contained in the collecting portion is discharged.

The fitting portion 30 is formed to have such a shape as to follow the shape of a part to which the body portion 10 is fitted. In the present embodiment, since the fitting portion 30 is fitted to an excretory part of the human body, the fitting portion 30 is formed to have such a shape as to follow the shape of an excretory part of the human body, for example, the shape of the penis P and is formed integrally with the body portion 10 at the inlet portion 21 side of the hollow portion 20 so as to be fitted to an excretory part of the human body. As illustrated in FIG. 1, the fitting portion 30 may be provided with an index 31 at a part on the outer side thereof. The index 31 may be provided at a part positioned upside in the up-down-left-right directions (direction to the head). Providing such an index 31 facilitates fitting in a correct direction.

The fitting portion 30 may be formed to have a condom shape and fitted to cover the penis P or may be applied in such a manner as to cover the external urethral orifice of the penis P and fitted to be adhered to the penis P using an adhesive agent or the like.

Further, for example, while the fitting portion 30 which is formed in such a manner as to cover the glans portion or the entirety of the penis P is fitted to the penis P, the fitting portion 30 may be covered from the outer side with an adhesive supporter, underwear, or the like.

In the present embodiment, a check valve 40 is disposed between the collecting portion 22 and the inlet portion 21 and prevents the material contained in the collecting portion 22 from flowing back to the inlet portion 21.

In the present embodiment, the check valve 40 is disposed near the fitting portion 30 side.

Figure 4:
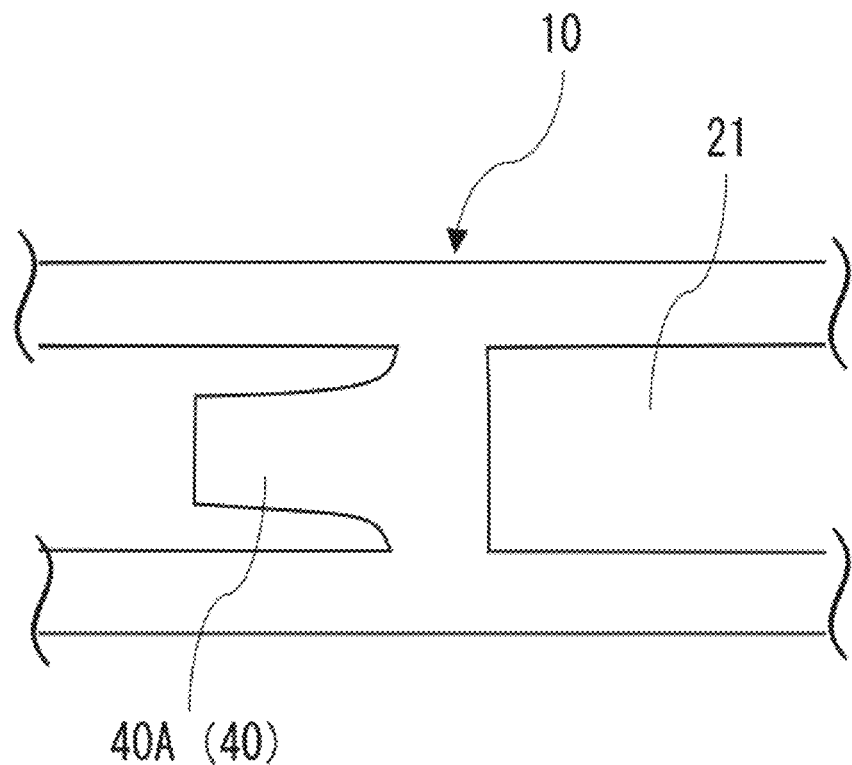
FIG. 4 is similarly a schematic diagram generally illustrating a configuration of a check valve of the collecting implement according to this embodiment.
Figure 5:
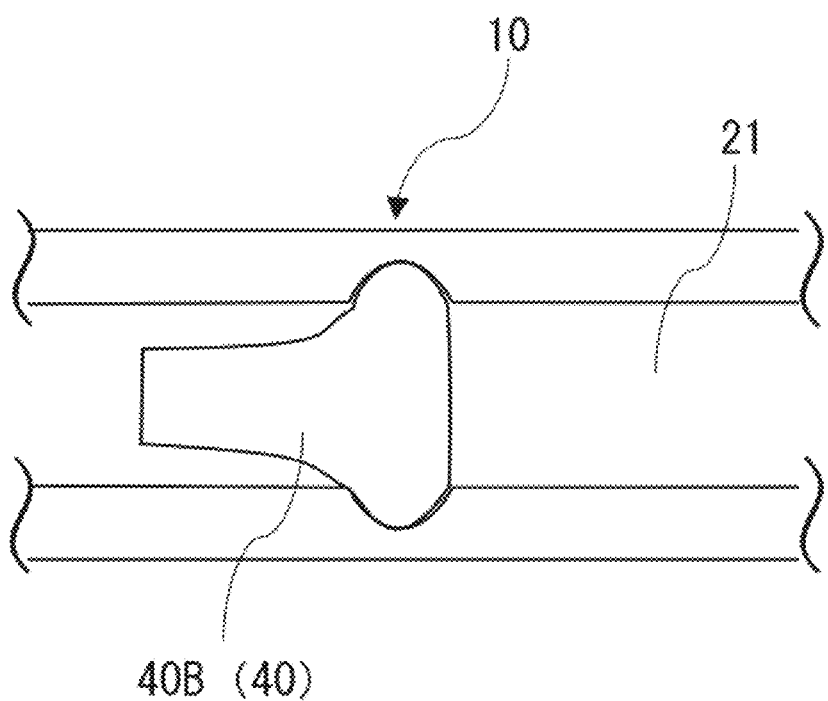
FIG. 5 is similarly a schematic diagram generally illustrating a configuration of the check valve of the collecting implement according to this embodiment.
Figure 6:
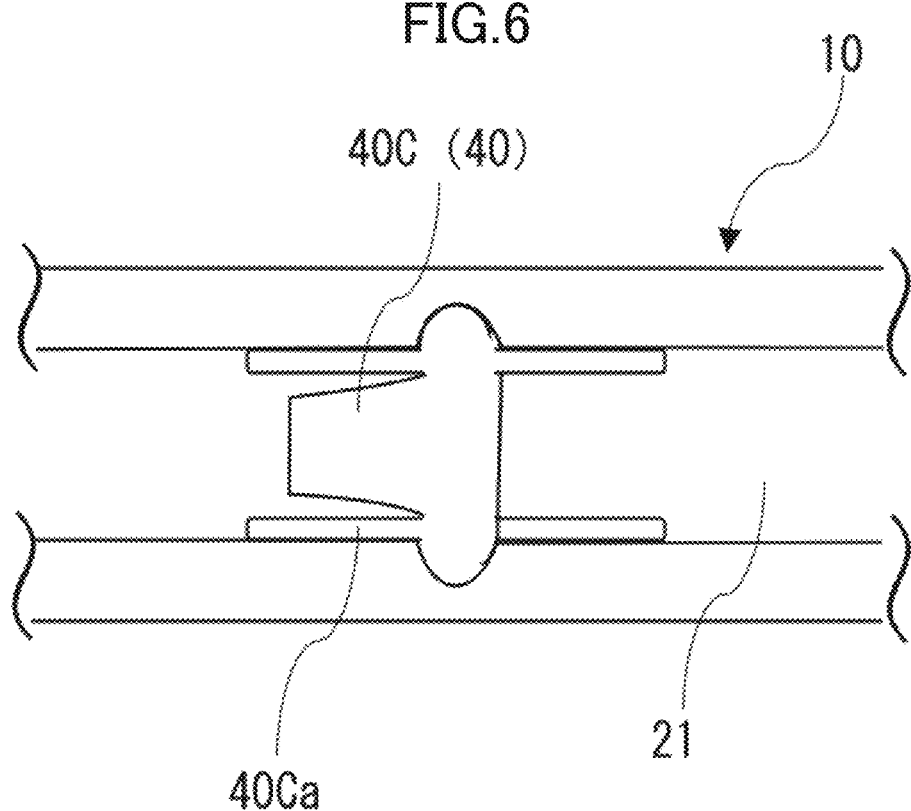
FIG. 6 is similarly a schematic diagram generally illustrating a configuration of the check valve of the collecting implement according to this embodiment.

FIG. 4 to FIG. 6 are each similarly a schematic diagram generally illustrating a configuration of the check valve 40. As illustrated in FIG. 4, the check valve may be a check valve 40A made of a resin which is formed, on the inner peripheral surface of the inlet portion 21, integrally with the inlet portion 21 or, as illustrated in FIG. 5, the check valve 40 may be a check valve 40B which is provided, on the inlet portion 21, separately from the inlet portion 21.

Further, as illustrated in FIG. 6, the check valve may be a check valve 40C which is provided, on the inlet portion 21, separately from the inlet portion 21 in which a valve cover 40Ca for protecting a body portion of the valve is formed and the valve cover 40Ca joins with the inner peripheral surface of the inlet portion 21.

In the present embodiment, for the check valve 40 (check valve 40A to check valve 40C), a variety of valves, such as a biomimetic artificial valve (cardiac valve, venous valve), a duckbill valve, or an umbrella valve may be employed.

In the present embodiment, the collecting implement 1 with such a configuration according to the present embodiment comprises a discharge mechanism which applies a force acting on the collecting portion 22 in which the material is contained so as to discharge the material through the outlet portion 23.

Figure 7:
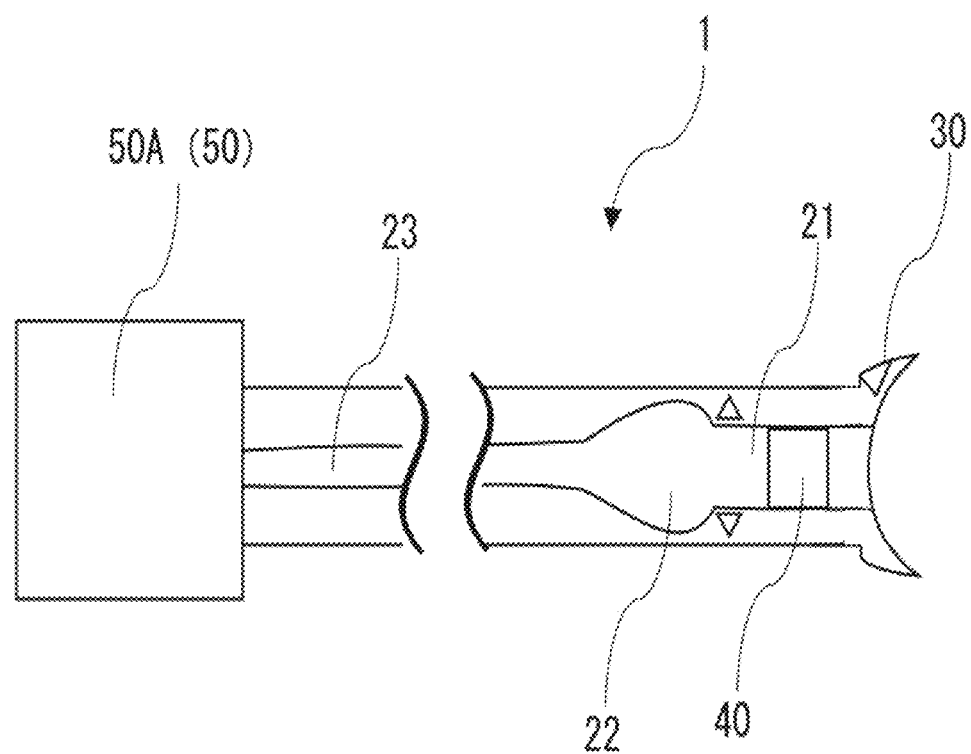
FIG. 7 is similarly a schematic diagram generally illustrating a discharge mechanism of the collecting implement according to this embodiment.
Figure 8:
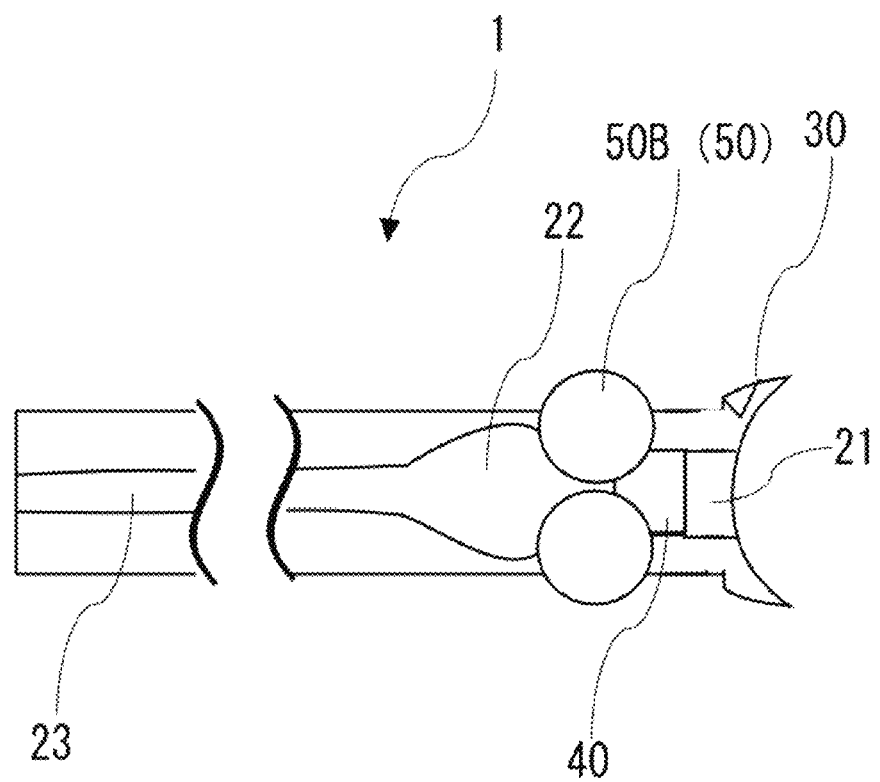
FIG. 8 is similarly a schematic diagram generally illustrating the discharge mechanism of the collecting implement according to this embodiment.

FIG. 7 and FIG. 8 are each similarly a schematic diagram generally illustrating a discharge mechanism. As illustrated in FIG. 7, a discharge mechanism 50 may be a suction device 50A which houses a suction pump for sucking a target object out of a target area.

In the present embodiment, the suction device 50A is provided to the body portion 10 via an unillustrated connection portion connected to the outlet portion 23 through the opening at the other end 10b side of the body portion 10, sucks the material out of the collecting portion 22 in which the material is contained, and allows the sucked material to be discharged through the outlet portion 23.

On the other hand, as illustrated in FIG. 8, the discharge mechanism 50 may be a pressing device 50B which is attached to the outer side of the body portion 10 and provided with a roller that is to be moved from the one end 10a side toward the other end 10b side of the body portion 10 while being pressed, thereby pressing the material contained in the collecting portion 22 out of the collecting portion 22.

In the present embodiment, the pressing device 50B presses the material contained in the collecting portion 22 out of the collecting portion 22 and the material is discharged through the outlet portion 23.

Further, the discharge mechanism 50 may be a pressing device in which an air bag into which high pressure air is to be introduced is attached at the outer side of the body portion 10 corresponding to the position at which the collecting portion 22 is disposed, and high pressure air is introduced into the air bag, thereby pressing the material contained in the collecting portion 22 out of the collecting portion 22.

Next, a method of use of the collecting implement 1 according to the present embodiment will be described.

Note that to describe the method of use of the collecting implement 1 according to the present embodiment, by way of example, a case in which the collecting implement is fitted to the penis P of the human body will be explained.

First, to attach the collecting implement 1 to the user, the penis P or the fitting portion 30 is coated with an adhesive agent or the like, and the fitting portion 30 is applied in such a manner as to cover the external urethral orifice of the penis P and adhered to the penis P, thereby achieving the attachment of the collecting implement 1.

The collecting implement 1 is made of an elastomer having a softness in which the hardness is extra low as well as a high stretchability so that to attach the collecting implement 1, the fitting portion 30 can be easily fitted to the penis P by the user to attach the collecting implement 1.

To attach the collecting implement 1, the user carries out the attachment while seeing the index 12 to confirm the direction in which the collecting portion 22 bulges.

After the attachment of the collecting implement 1, while confirming the index 12, the user bends in advance, at the bent portion 11, the body portion 10 on the other end 10b side toward the one end 10a side. In the present embodiment, the body portion 10 has a softness in which the hardness is extra low, while the outlet portion 23 is formed to be sufficiently thick in relation to the collecting portion 22 so that a simple operation of bending the body portion 10 allows the outlet portion 23 to be closed.

Thus, even a weak person, such as an elderly person or a sick person, can easily close the outlet portion 23.

When the user urinates while the collecting implement 1 is attached, the urine which is the material flows through the fitting portion 30, the inlet portion 21, and the check valve 40 disposed at the inlet portion 21 then into the collecting portion 22 and is contained therein.

In the present embodiment, after the urine flows into and is contained in the collecting portion 22, for the collecting portion 22, the thin part of the body portion 10 bulges toward the outer side of the body portion 10 and the outside of the human body of the user so that the bulge portion 22a is formed, thereby securing a sufficient area for containing the urine introduced from the inlet portion 21.

Then, the body portion 10 on the other end 10b side is bent at the bent portion 11 toward the one end 10a side and the outlet portion 23 is thus closed, which prevents the urine contained in the collecting portion 22 from unintentionally being discharged through the outlet portion 23.

On the other hand, even when an external pressure is applied to the body portion 10 and the urine collected in the collecting portion 22 is accordingly pressed, the check valve 40 disposed at the inlet portion 21 prevents the urine from flowing back into the fitting portion 30.

To discharge the urine contained in the collecting portion 22, the body portion 10 bent at the bent portion 11 toward the one end 10a side is developed toward the urinal and the collecting portion 22 is pressed so that the urine contained in the collecting portion 22 is discharged.

Thus, the urine contained in the collecting portion 22 can be discharged while the collecting implement 1 is attached to the user in a standing posture. Therefore, it is expected to decrease a mental or psychological burden of excretion.

On the other hand, to discharge the urine contained in the collecting portion 22, the discharge mechanism 50 may be attached to the body portion 10 so as to discharge the urine contained in the collecting portion 22 through the outlet portion 23.

Thus, in the collecting implement 1 according to the present embodiment, the inlet portion 21 into which the urine is introduced and the collecting portion 22 which collects and contains the urine are formed integrally as the hollow portion 20 in a seamless manner in the body portion 10, thereby restraining the urine introduced or contained from leaking out.

Further, the body portion 10 having the hollow portion 20 in which the inlet portion 21 and the collecting portion 22 are integrally formed in a seamless manner is made of an elastomer having a softness in which the hardness is extra low as well as a high stretchability so that no hard part interposes.

Thus, no hard part causes comfortability or mobility for the user to decrease and accordingly a good feeling during use is achieved.

Second Embodiment

Next, a second embodiment of the present invention will be described with reference to FIG. 9.

Figure 9:
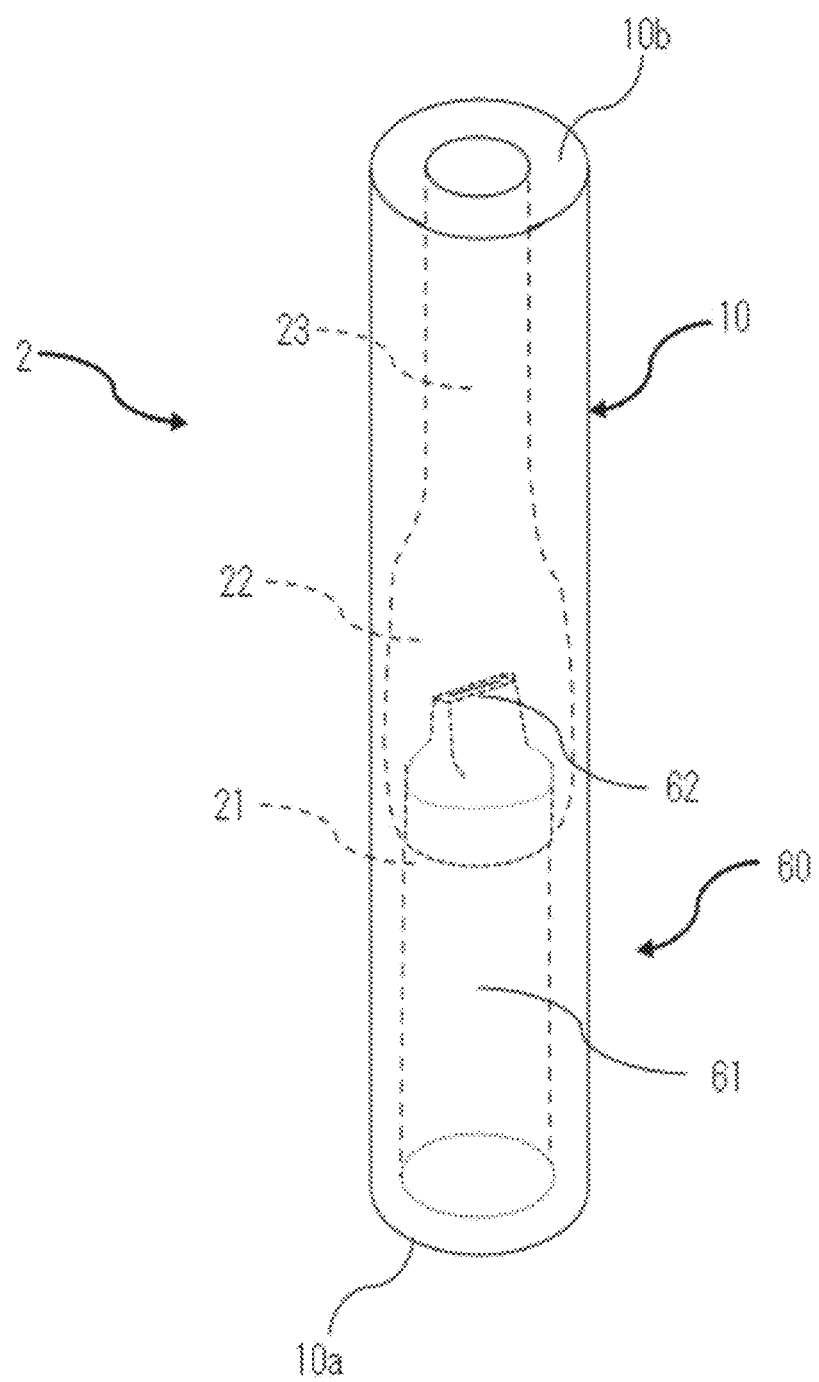
FIG. 9 is a schematic diagram generally illustrating a collecting implement according to a second embodiment of the present invention.

FIG. 9 is a schematic diagram generally illustrating a collecting implement according to the present embodiment.

Note that, in FIG. 9, components similar to those according to the first embodiment are denoted by the same reference signs and a description thereof is omitted.

As illustrated, a collecting implement 2 comprises as main components the body portion 10 and an attachment portion 60 attached to the body portion 10.

In the present embodiment, the attachment portion 60 has a substantially cylindrical shape, the attachment portion 60 comprising a fitting portion 61 formed on one side and a check valve 62 formed on the other side in which the fitting portion 61 and the check valve 62 are integrally formed.

The fitting portion 61 is formed to have such an optional shape as to follow an excretory part of the human body and, in the present embodiment, is formed to have a condom shape to cover the penis.

The check valve 62 is configured to prevent the urine which is the material introduced from the inlet portion 21 and contained in the collecting portion 22 from flowing back to the inlet portion 21 and, in the present embodiment, for the check valve 62, a variety of valves, such as a biomimetic artificial valve (cardiac valve, venous valve), a duckbill valve, or an umbrella valve may be employed.

In the present embodiment, the attachment portion 60 tightly fits to the inlet portion 21 in the hollow portion 20 of the body portion 10 so as to be attached to the body portion 10.

When the collecting implement 2 is attached to the user, the fitting portion 61 is tightly fitted to the penis, while the attachment portion 60 tightly fits to the body portion 10, which restrains the urine contained in the collecting portion 22 from leaking out when the user urinates while the collecting implement 2 is attached to the user.

Third Embodiment

Next, a third embodiment of the present invention will be described with reference to FIG. 10 and FIG. 11.

Figure 10:
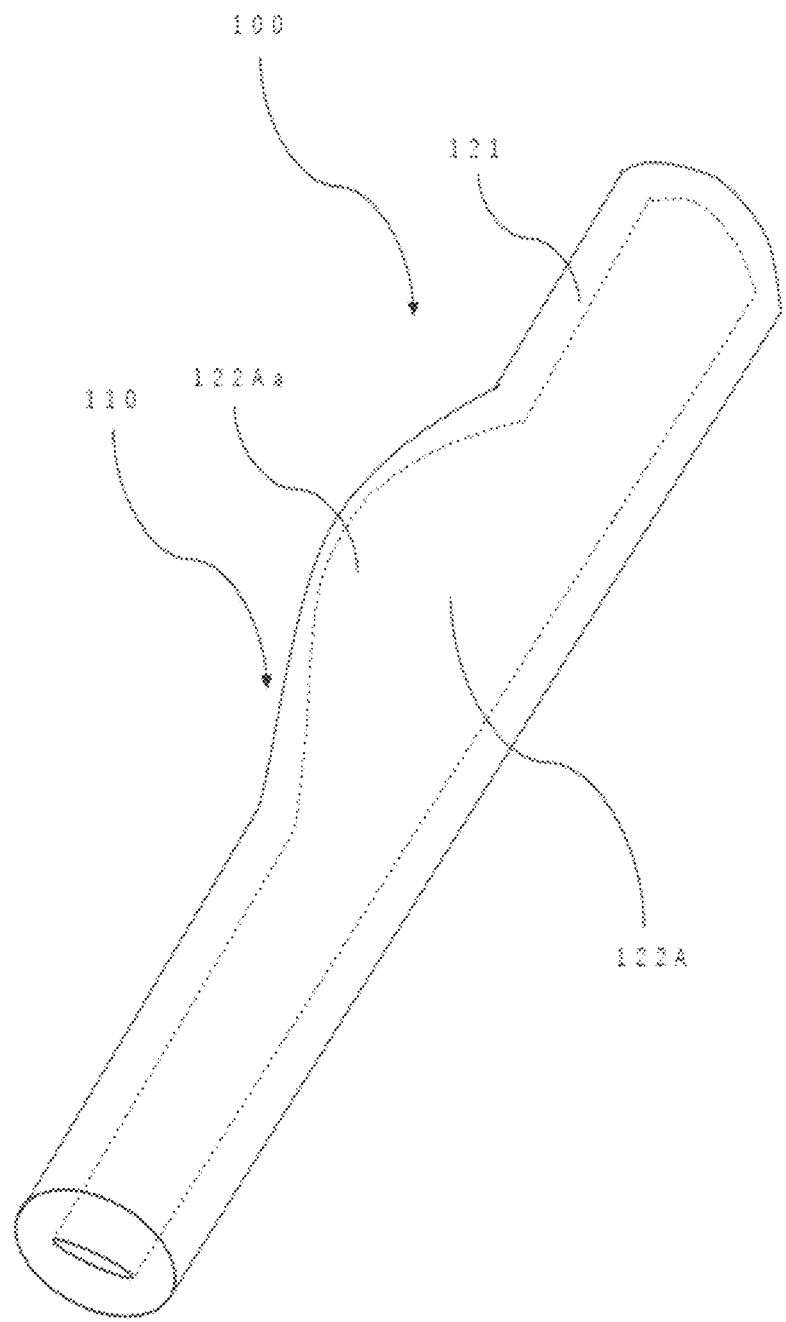
FIG. 10 is a perspective view illustrating a collecting implement according to a third embodiment of the present invention.
Figure 11:
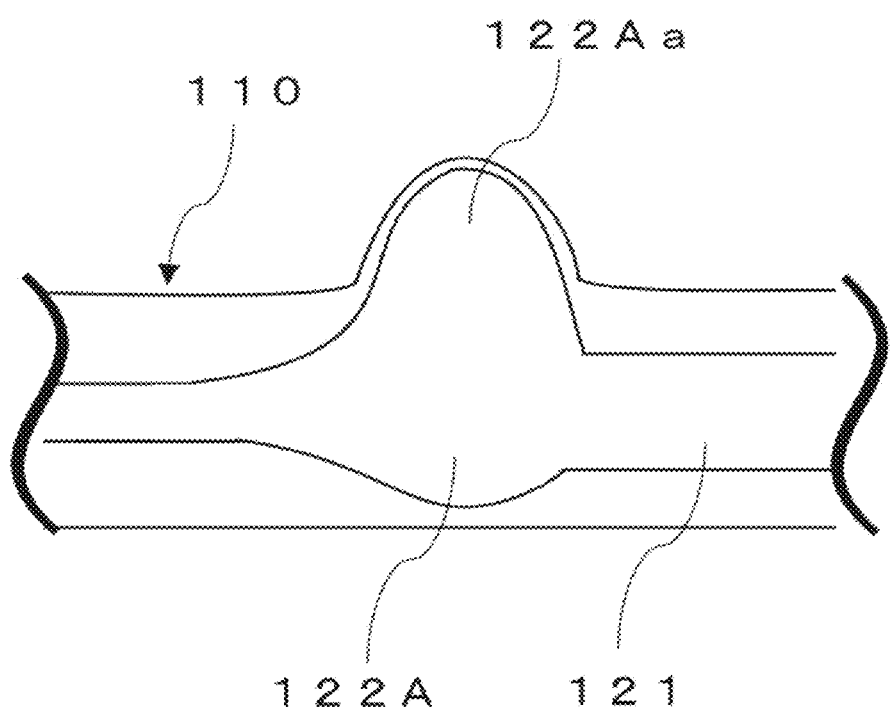
FIG. 11 is similarly a side cross-sectional view generally illustrating the collecting implement according to this embodiment.

FIG. 10 is a perspective view illustrating a collecting implement according to the third embodiment of the present invention. FIG. 11 is similarly a side cross-sectional view generally illustrating the collecting implement according to the present embodiment.

In a collecting implement 100 according to the third embodiment, the predetermined part protrudes in a convex manner further outward than the other part of a collecting portion 122.

The third embodiment differs from the first embodiment or the second embodiment in that the predetermined part of the collecting portion 122 protrudes outward. As illustrated in FIG. 10 and FIG. 11, a collecting portion 122A of the collecting implement 100 has a protrusion part 122Aa. The protrusion part 122Aa is a convex protrusion and protrudes outward from a body portion 110. Further, the protrusion part 122Aa is a part formed to be thin of the body portion 110 (predetermined part). In the present embodiment, the protrusion part 122Aa corresponds to the entirety of the predetermined part. Note that the predetermined part 122Aa may be a part corresponding to a part of the predetermined part.

Further, the protrusion part 122Aa may be provided with a bridge such that the shape of the protrusion part 122Aa is maintained.

Thus, the collecting portion 122A is provided with the protrusion part 122Aa in advance, thereby securing a large and sufficient area for containing the material introduced from an inlet portion 121.

Figure 12:
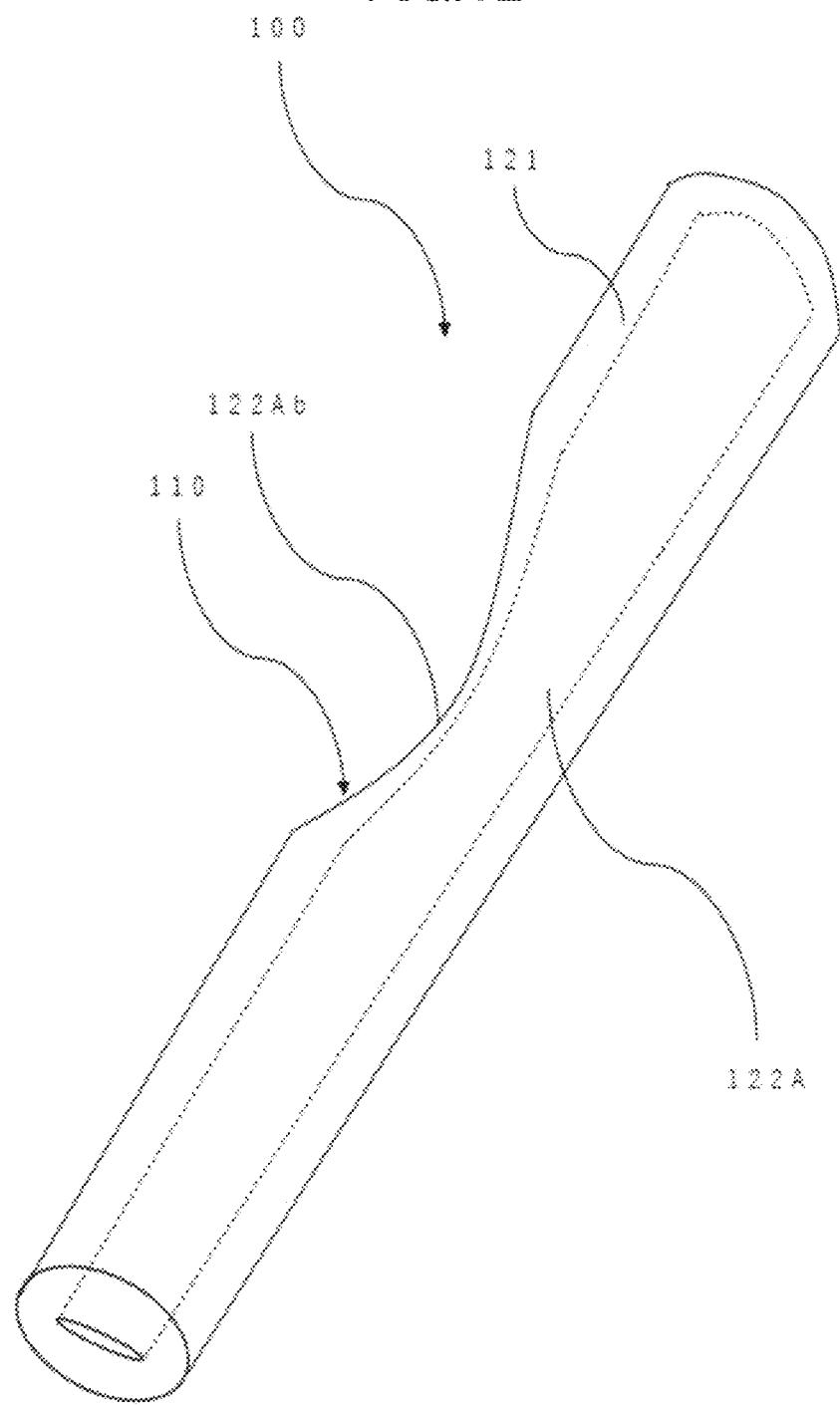
FIG. 12 is a perspective view illustrating a modification example of the third embodiment.

Note that FIG. 12 is a perspective view illustrating a modification example of the third embodiment. As illustrated in FIG. 12, in place of the protrusion part 122Aa according to the third embodiment, a sunken part 122Ab may be formed. The sunken part 122Aa is a part in which the predetermined part of the collecting portion 122A sinks inward in a concave manner.

Similarly to the configuration in which the protrusion part 122Aa is formed, the configuration in which such a sunken part 122Ab is formed allows the bulge toward the outer side of the body portion 110 when the material introduced from the inlet portion 121 is contained. Thereby, a large and sufficient area for the collecting portion 122A is secured.

Fourth Embodiment

Next, a fourth embodiment of the present invention will be described with reference to FIG. 13 to FIG. 18.

Figure 13:
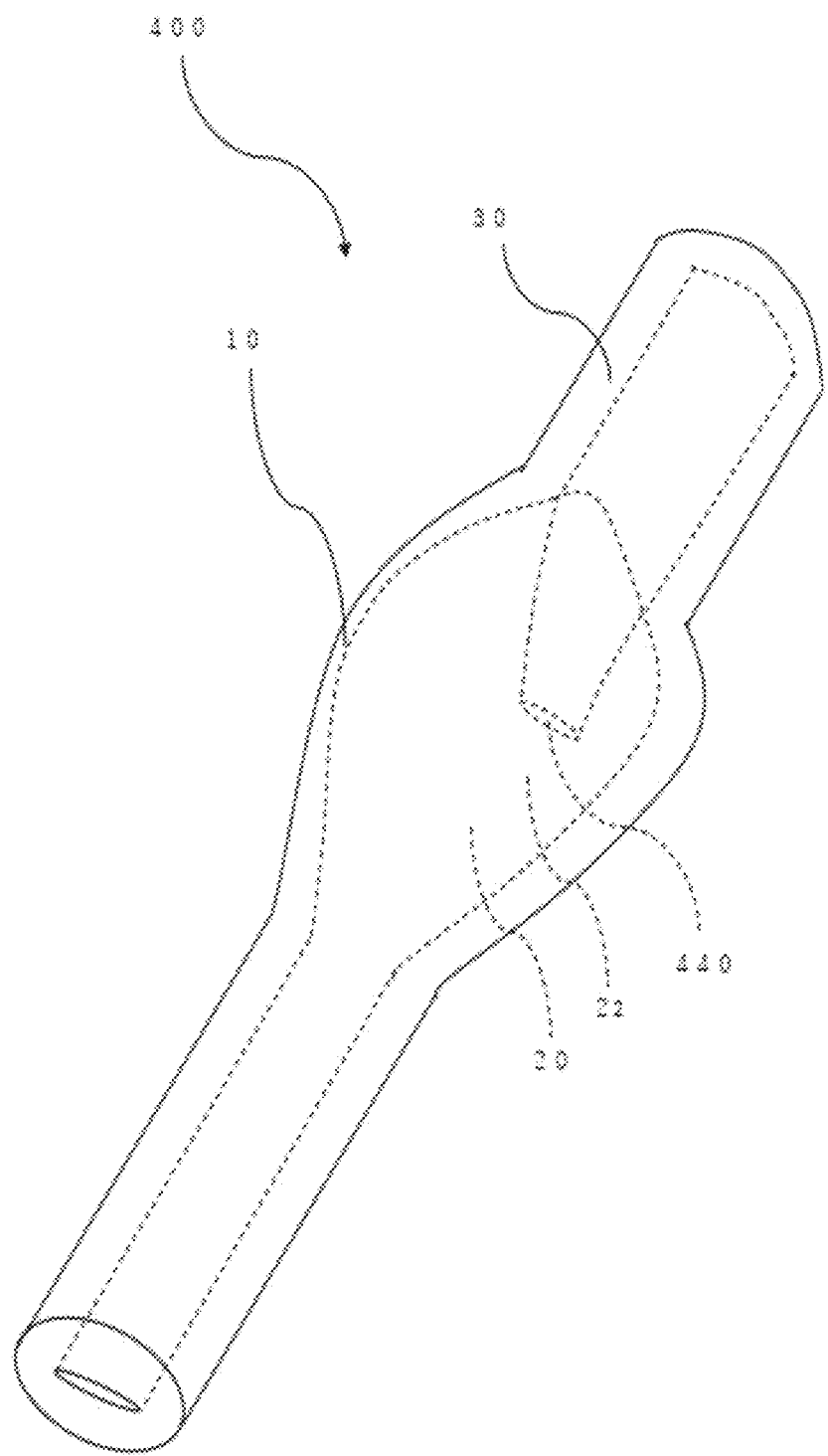
FIG. 13 is a perspective view illustrating a collecting implement according to the third embodiment of the present invention.
Figure 14:
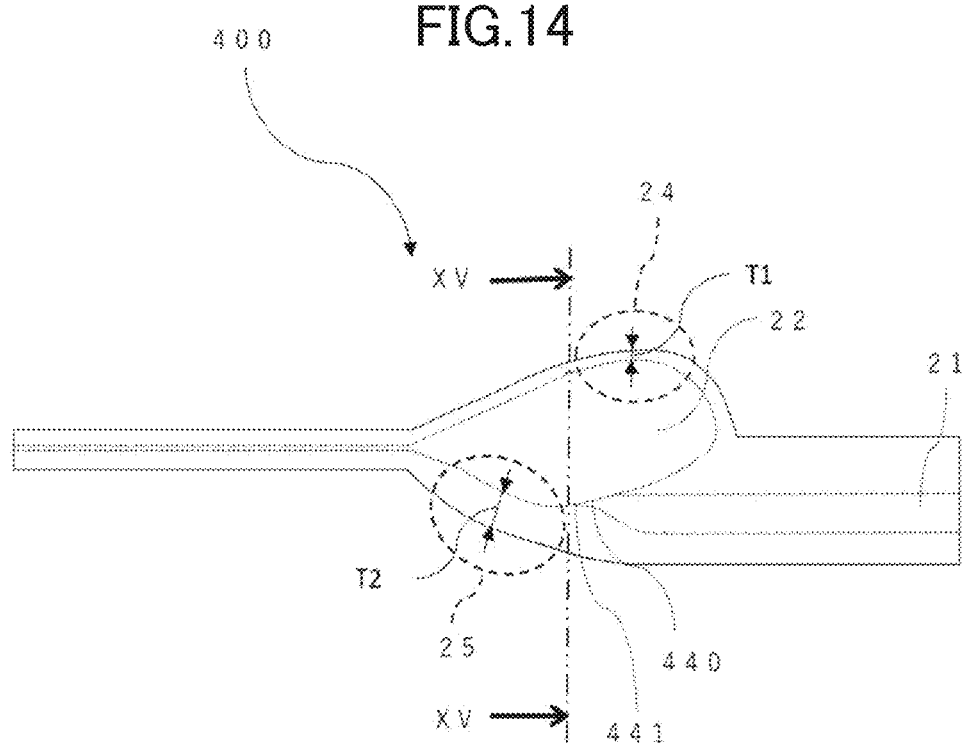
FIG. 14 is similarly a side cross-sectional view generally illustrating the collecting implement according to this embodiment.
Figure 15:
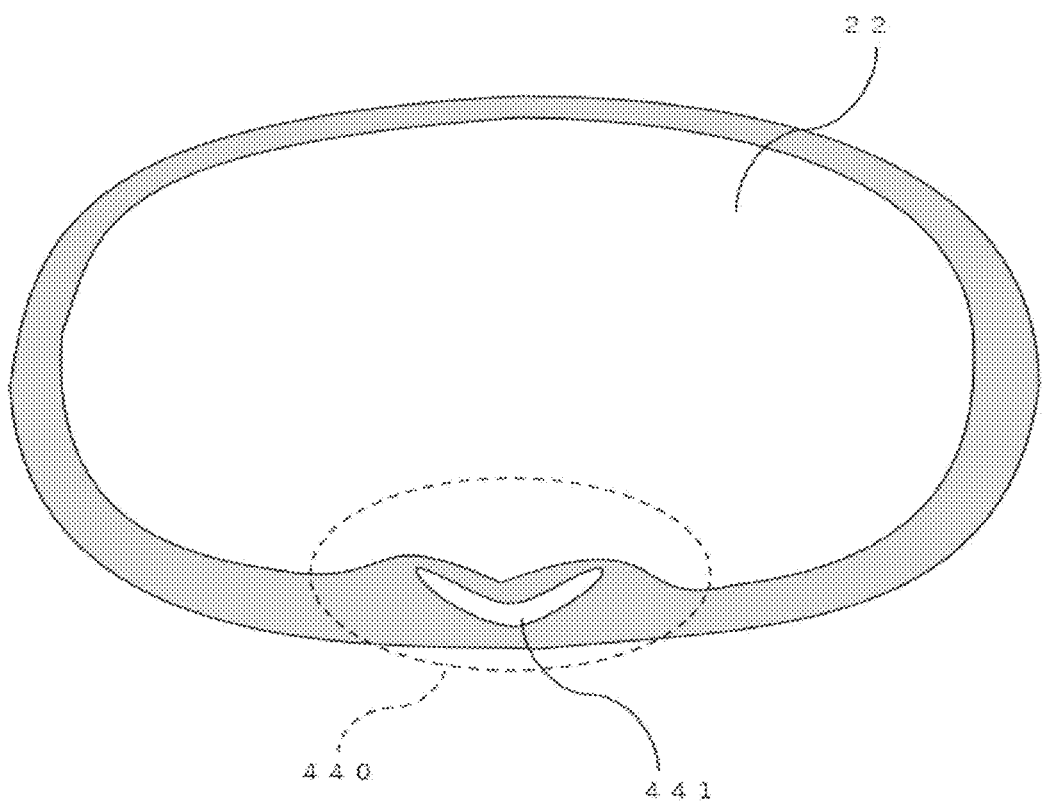
FIG. 15 is a cross-sectional view along line XV-XV of FIG. 14 when a check valve is closed.
Figure 16:
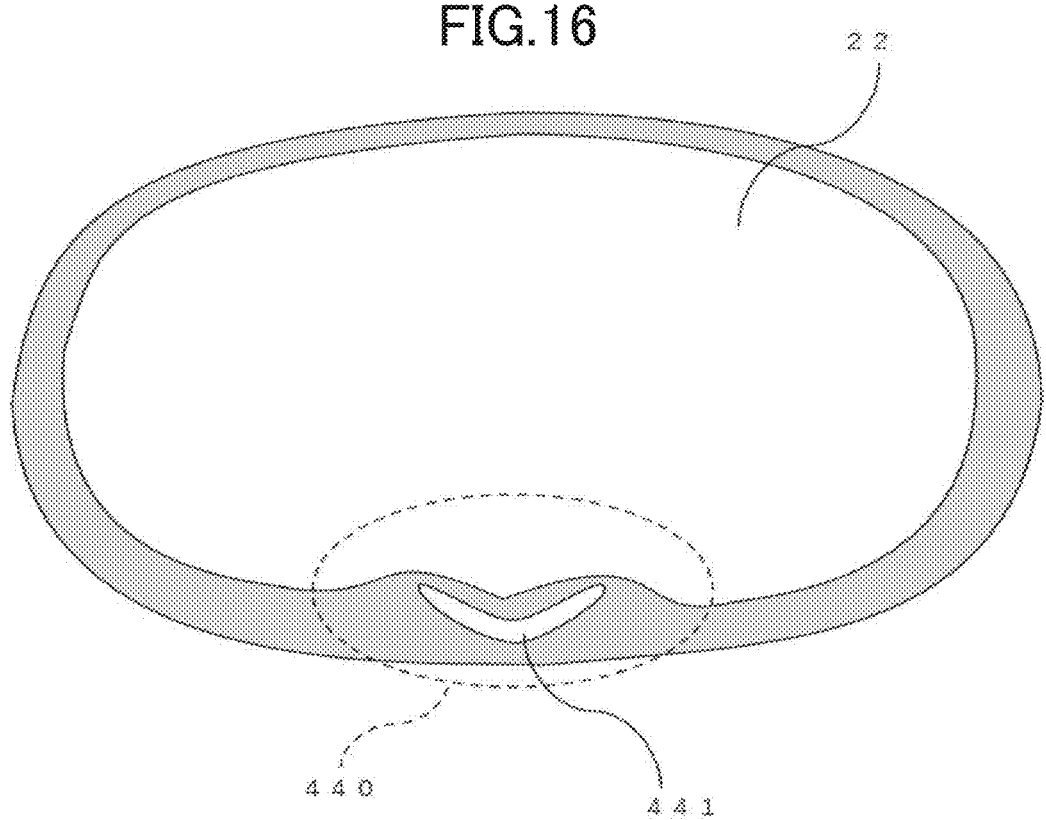
FIG. 16 is a cross-sectional view along line XV-XV of FIG. 14 when the check valve is open.
Figure 17:
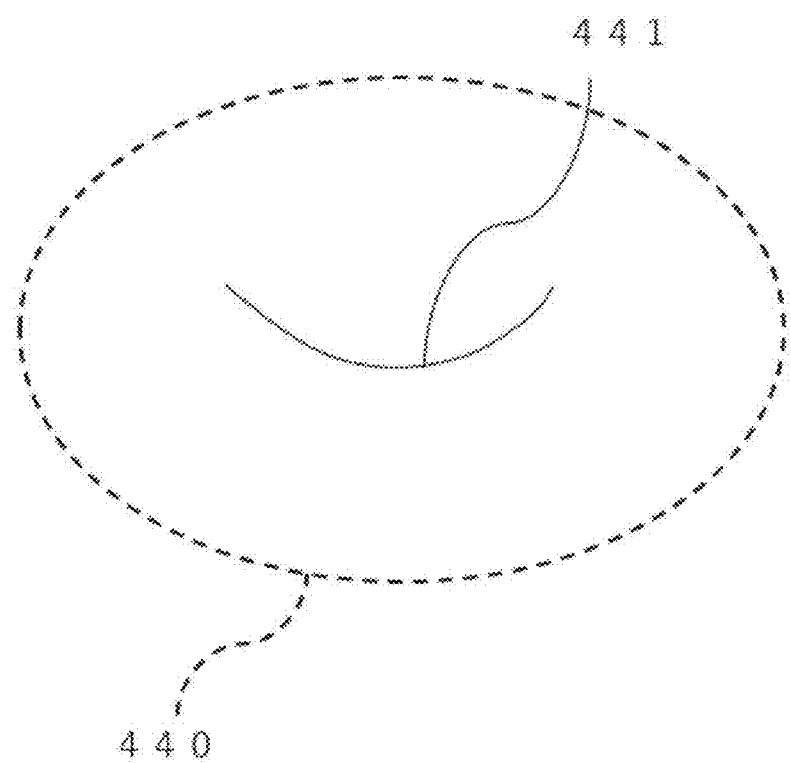
FIG. 17 is a partially enlarged view illustrating the check valve of FIG. 15 in an enlarged manner.
Figure 18:
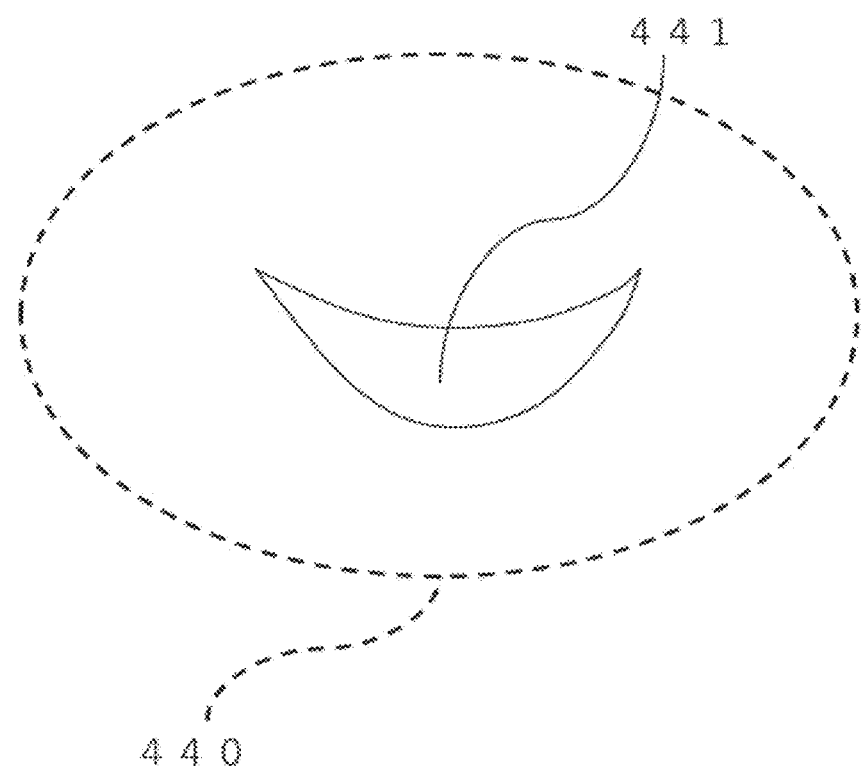
FIG. 18 is a partially enlarged view illustrating the check valve of FIG. 16 in an enlarged manner.

FIG. 13 is a perspective view illustrating a collecting implement according to the third embodiment of the present invention. FIG. 14 is similarly a side cross-sectional view generally illustrating the collecting implement according to this embodiment. FIG. 15 is a cross-sectional view along line XV-XV of FIG. 14 when a check valve is closed, and FIG. 16 is a cross-sectional view along line XV-XV of FIG. 14 when the check valve is open. Further, FIG. 17 is a partially enlarged view illustrating the check valve of FIG. 15 in an enlarged manner, and FIG. 18 is a partially enlarged view illustrating the check valve of FIG. 16 in an enlarged manner.

Similarly to the collecting implement 1 according to the first embodiment, a collecting implement 400 according to the present embodiment comprises as main components the body portion 10, the hollow portion 20 formed in the body portion 10, and the fitting portion 30 formed with the body portion 10.

In the collecting implement 400 according to the present embodiment, a thickness T1 of the predetermined part 24 is, for example, 3 mm to 4.5 mm, preferably 3.5 mm. Such a thickness T1 allows the predetermined part 24 to expand more easily than the other part. Further, the collecting portion 22 is provided with a thick part 25 which is thicker than the other part. The thick part 25 may be the entirety of the part other than the predetermined part. A thickness T2 of the thick part 25 is, for example, 5 mm to 6 mm, preferably 5.5 mm. It is more difficult for the thick part 25 to stretch than for the other part. It is difficult for the thick part 25 to expand when the interior of the collecting portion 22 is in a pressurized state. Thus, it is considered that when the thick part 25 comes into contact with and is fitted to the body of the user, the user is unlikely to feel uncomfortable even when the collecting portion 22 expands.

Note that, in the collecting portion 22, an amount of stretch of the predetermined part 24 is, for example, 1.8 times to 2.2 times an amount of stretch of the thick part 25. Further, the ratio of the thickness T1 of the predetermined part 24 to the thickness T2 of the thick part 25, i.e., T1/T2 is, for example, 0.6 to 0.7. The thickness T1 of the predetermined part 24 is, for example, 3.5 mm and the thickness T2 of the thick part 25 is, for example, 5.5 mm.

Such a relationship allows the predetermined part 24 to expand outward when the urine or the feces are stored in the interior of the collecting portion 22 and there occurs a state in which a pressure is applied from the interior to the exterior (pressurized state). Thereby, the volume of the interior of the collecting portion 22 increases and the capacity to contain the urine or the feces increases.

Further, the collecting implement 400 according to the present embodiment comprises a check valve 440 in place of the check valve 40 according to the first embodiment. The check valve 440 is disposed between the collecting portion 22 and the inlet portion 21 and prevents the material contained in the collecting portion 22 from flowing back to the inlet portion 21. The check valve 440 is integrally formed with the inlet portion 21 and the collecting portion 22 in the body portion 10 in a seamless manner.

The check valve 440 has an opening part 441. The opening part 441 is open when a pressure is applied in a direction from the inlet portion 21 to the collecting portion 22 or is closed otherwise. Note that also when a pressure is not applied in a direction from the inlet portion 21 to the collecting portion 22, the opening part 441 may be not completely closed or may be slightly open. This is because it is considered that even when the opening part 441 is slightly open, the surface tension of the fluid itself, such as the urine or the feces, prevents a back flow in a direction from the collecting portion 22 to the inlet portion 22. Then, the opening part 441 is closed when a pressure is applied in a direction from the collecting portion 22 to the inlet portion 21.

The opening part 441 of the check valve 440 is positioned along the inner wall side surface of the collecting portion 22. Such an arrangement allows the check valve 440 to be supported on the inner wall side surface of the collecting portion 22. Thus, in the present embodiment, even when the check valve 440 is made from a stretchable elastic member (in particular, made of a soft material), the strength of the check valve 440 is maintained and valve functions are carried out.

Further, the opening part 441 of the check valve 440 is, for example, a slit. As illustrated in FIG. 15 and FIG. 16, the opening part 441 is, for example, a U-shaped slit. In this case, the U-shaped slit may be configured such that a protrusion part between both end parts is oriented toward either the collecting portion 22 or the inlet portion 21, and may include a V-shaped slit, a C-shaped slit, or the like. The slit of the opening part 441 is preferably configured such that the protrusion part is oriented toward the inlet portion 21 (fitting portion 30) side. Such a shape can securely prevent a back flow from the collecting portion 22 to the inlet portion 21 while utilizing also the surface tension of the urine or the feces.

Next, an operation of the check valve 440 of the collecting implement 400 according to the present embodiment will be described. When the urine is discharged from the genital organ of the user, the urine flows through the inlet portion 21 in a direction of the collecting portion 22. When a pressure is not applied, the opening part 441 of the check valve 440 is closed or slightly open. Note that it is considered that even when the opening part 441 is slightly open, if a certain amount or more of the urine is not stored over the opening part 441 of the check valve 440, the surface tension of the urine itself prevents the urine from passing the opening part 441. On the other hand, the opening part 441 is closed in a normal state. It is considered that when a certain amount or more of the urine is stored over the opening part 441, the weight of the urine itself (or a pressure difference between the inlet portion 21 and the collecting portion 22) causes a pressure to be applied to the opening part 441 of the check valve 440 in a direction from the inlet portion 21 to the collecting portion 22. It is considered that such an application of a pressure allows the opening part 441 to be open. It is considered that the opening part 441 is allowed to be open so that the urine flows from the inlet portion 21 into the collecting portion 22. It is considered that the urine flowing into the collecting portion 22 is stored in the collecting portion 22.

On the other hand, it is considered that when the urine stored in the collecting portion 22 is pressed and a pressure is accordingly applied to the opening part 441 of the check valve 440 in a direction from the collecting portion 22 to the inlet portion 21, the opening part 441 is not made to be open. Rather, it is considered that when a pressure is applied in a direction from the collecting portion 22 to the inlet portion 21, an elastic force is applied to the opening part 441 and the opening part 441 is accordingly closed firmly. Thus, it is considered that the urine once flowing into the collecting portion 22 is prevented from flowing back into the inlet portion 21.

Fifth Embodiment

Next, a fifth embodiment of the present invention will be described with reference to FIG. 19.

Figure 19:
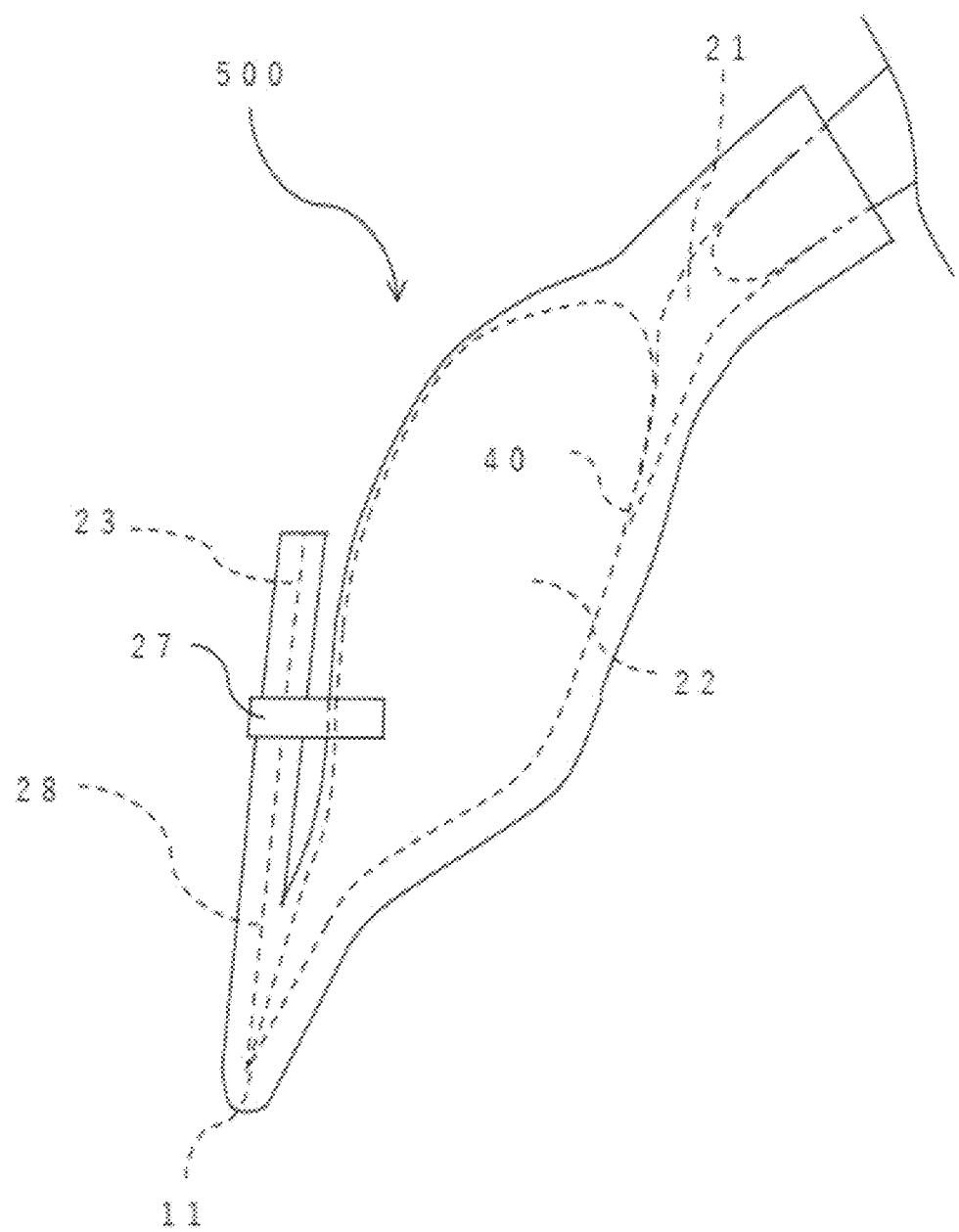
FIG. 19 is a side view illustrating a collecting implement according to a fifth embodiment of the present invention.

FIG. 19 is a side view illustrating a collecting implement according to the fifth embodiment of the present invention.

In a collecting implement 500 according to the present embodiment, the outlet portion 23 allows the urine or the feces stored in the collecting portion 22 to flow out to the exterior of the body portion 10.

In the present embodiment, the outer side surface of the body portion 10 is provided with a support band 27. The support band 27 has a belt shape and is formed by, for example, a stretchable elastic member. Note that the support band 27 is made of preferably a stretchable material which is preferably a rubber, a fiber, or the like. The support band 27 may be made of, for example, the same material as the body portion 10. Note that the support band 27 may be made of the other material. The both ends of the support band 27 are fixed to the outer side of the collecting portion 22, for example, using an adhesive agent or welding. An intermediate portion of the support band 27 is not fixed to the outer side of the collecting portion 22. Note that the support band 27 may be formed integrally with the body portion 10. At the intermediate portion of the support band 27, a gap between the support band 27 and the collecting portion 22 is formed. The collecting portion 22 and the support band 27 are formed by a stretchable elastic member so that the gap can be expanded. Into the gap, the outlet portion 23 is inserted, whereby the outlet portion 23 is fixed.

In the present embodiment, the outlet portion 23 has a discharge path 28 between the collecting portion 22 and the other end portion 10b (FIG. 9). As illustrated in FIG. 19, at least a part of the outlet portion 23 (in this case, the downstream side than the bent portion 11) is supported in a posture upward from below in a perpendicular direction from the upstream side toward the downstream side of the discharge path 28 (in a direction from the collecting portion 22 to the outlet portion 23). Note that from the upstream side toward the downstream side of the discharge path 28 means a direction of discharge of the urine or the feces in view of the collecting implement 500 as a whole.

The outlet portion 23 is inserted and fixed between the outer side of the collecting portion 22 and the support band 27. Thereby, the outlet portion 23 is held at the downstream side of the outlet portion 23 than the bent portion 11 in a posture upward from below in a perpendicular direction from the upstream side toward the downstream side of the discharge path 28.

Sixth Embodiment

Next, a sixth embodiment of the present invention will be described with reference to FIG. 20 and FIG. 21.

Figure 20:
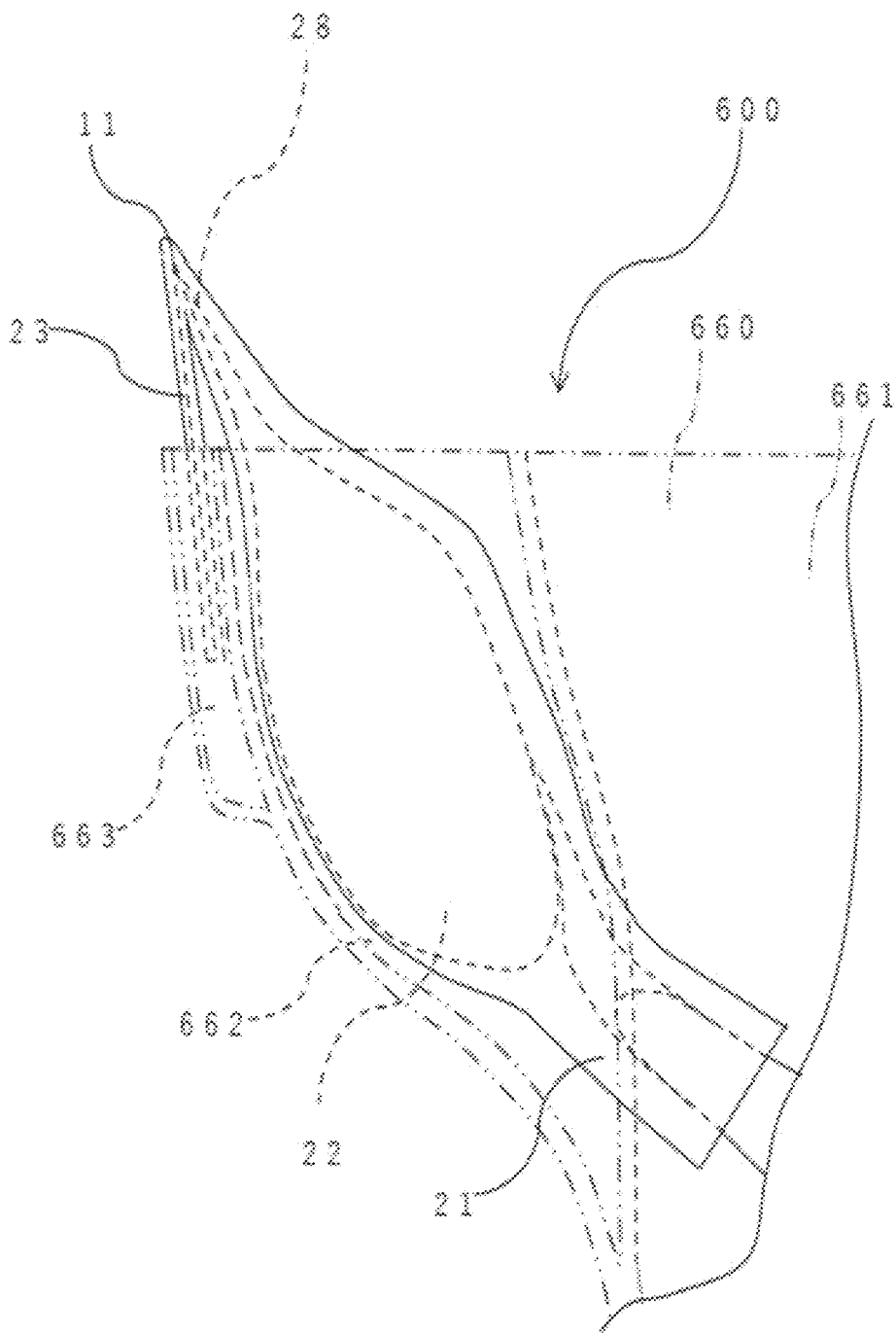
FIG. 20 is an explanatory diagram illustrating a state in which a collecting implement according to a sixth embodiment is attached.
Figure 21:
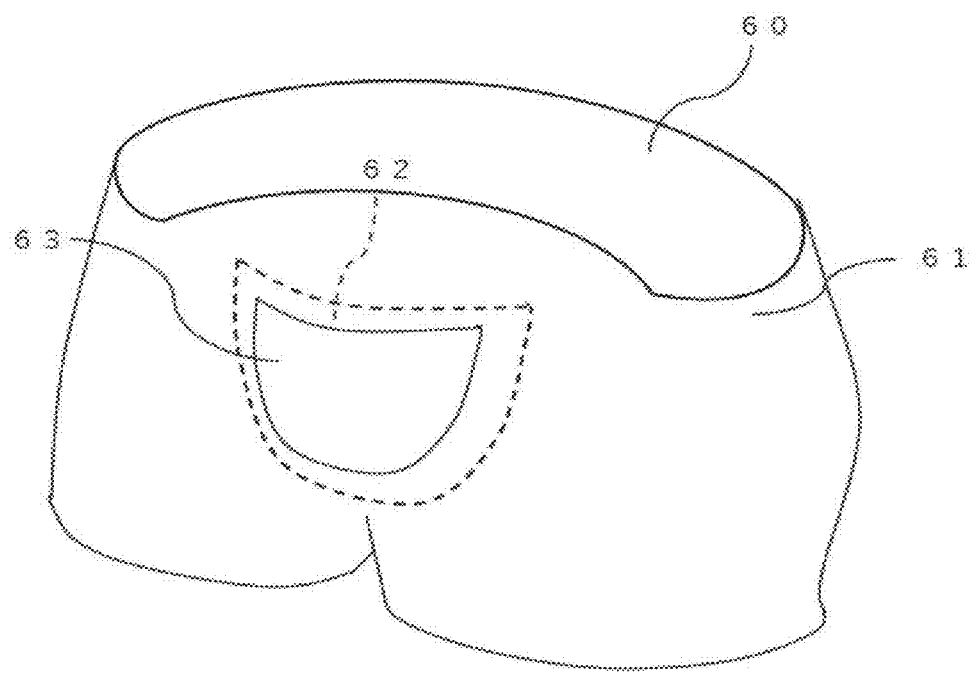
FIG. 21 is a perspective view illustrating a support member of the collecting implement according to the sixth embodiment.

FIG. 20 is an explanatory diagram illustrating a state in which a collecting implement according to the sixth embodiment is attached. Further, FIG. 21 is a perspective view illustrating a support member of the collecting implement according to the sixth embodiment. Note that in FIG. 20, the support member from the collecting implement is indicated by two-dot chain lines.

A collecting implement 600 according to the present embodiment further comprises a support member 660. The support member 660 is a member to be attached to the body of the user. The support member 660 has a body attachment part 661 which is attached to the body, a collecting portion support part 662 for supporting the collecting portion 22, and an outlet portion support part 663 for supporting the outlet portion 23.

The body attachment part 661 is of a type of, for example, an underwear. Note that the body attachment part 661 may be of a type of a belly band. The collecting portion support part 662 is fixed to the body attachment part 661 in such a manner as to be disposed at the inner side (at the side in contact with the body of the user) of the body attachment part 661. The collecting portion support part 662 has a pocket shape. The collecting portion 662 is accommodated in the inner side of such a collecting portion support part 662. Further, the outlet portion support part 663 is fixed to the body attachment part 661 in such a manner as to be disposed at the outer side (at the side not in contact with the body of the user) of the body attachment part 661. The outlet portion support part 663 also has a pocket shape. The end part of the outlet portion 623 is accommodated in the inner side of such an outlet portion support part 663 so that the outlet portion 623 is supported. Thus, the end part (a part at which the urine or the feces exits) of the outlet portion 623 is accommodated in a space with which the body does not come into contact and accordingly a hygienic state of the user is maintained to be good. Further, the end part of the outlet portion 623 is accommodated in the inner side of the outlet portion support part 663, which provides a hygienic appearance.

Seventh Embodiment

Next, a seventh embodiment of the present invention will be described with reference to FIG. 22.

Figure 22:
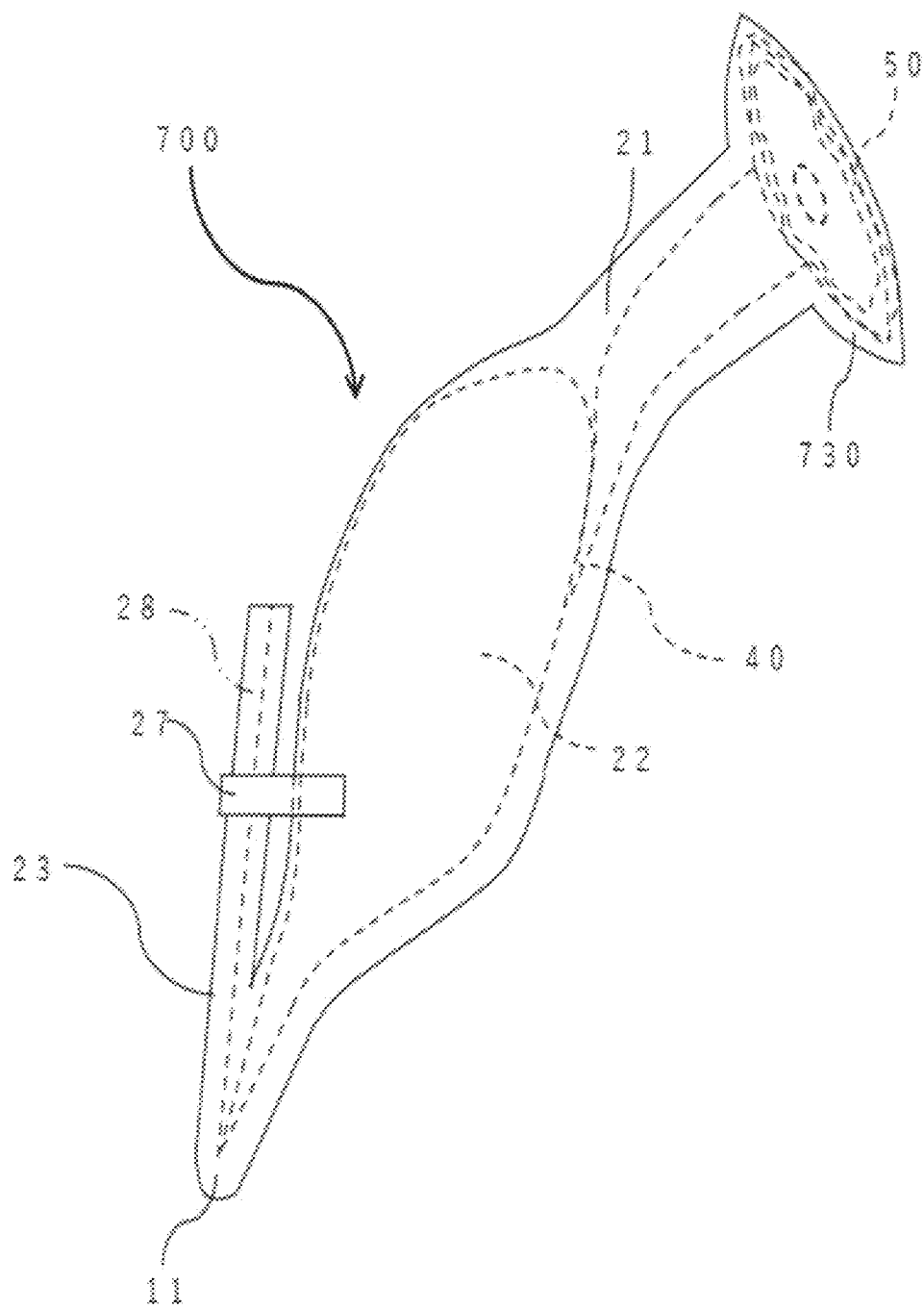
FIG. 22 is an explanatory diagram illustrating a state in which a collecting implement according to a seventh embodiment is attached.

FIG. 22 is an explanatory diagram illustrating a state in which a collecting implement 700 according to the seventh embodiment is attached.

The collecting implement 700 according to the present embodiment comprises a fitting portion 730 in place of the fitting portion 30 according to the first embodiment. The fitting portion 730 is formed to have such a shape as to follow the shape of a part to which the body portion 10 is fitted. In the first embodiment, the fitting portion 30 is formed to have such a shape as to follow, for example, the penis P, whereas the fitting portion 730 is formed to have such a shape as to follow, for example, the shape of the genital part (the urethral orifice or the anus) of the user. For example, the fitting portion 730 is formed to have a bowl shape. Note that the fitting portion 730 may have not only a bowl shape but also a plate shape. The fitting portion 730 is arranged around the genital part (the urethral orifice or the anus) of the user. Further, an adhesive agent 50 is applied on a part of the fitting portion 730 which comes into contact with the body.

The fitting portion 730 is adhered to the surface of the body using the adhesive agent 50 which is applied to around the genital part of the user. Thus, the fitting portion 730 can be used even when, in contrast to the fitting portion 30 according to the first embodiment, the fitting portion 730 does not fit to the genital part.

Note that when the fitting portion 730 is attached to the user, the bowl-shaped or plate-shaped fitting portion 730 is pressed against a part to be attached. Since the fitting portion 730 has a low hardness, the fitting portion 730 can be easily adjusted to the shape of the part to be attached. Thus, the attachment is achieved without the sensation of pain for the user or without a leakage of the urine or the feces from a gap between the fitting portion 730 and the part to be attached.

Eighth Embodiment

Next, an eighth embodiment of the present invention will be described with reference to FIG. 23.

Figure 23:
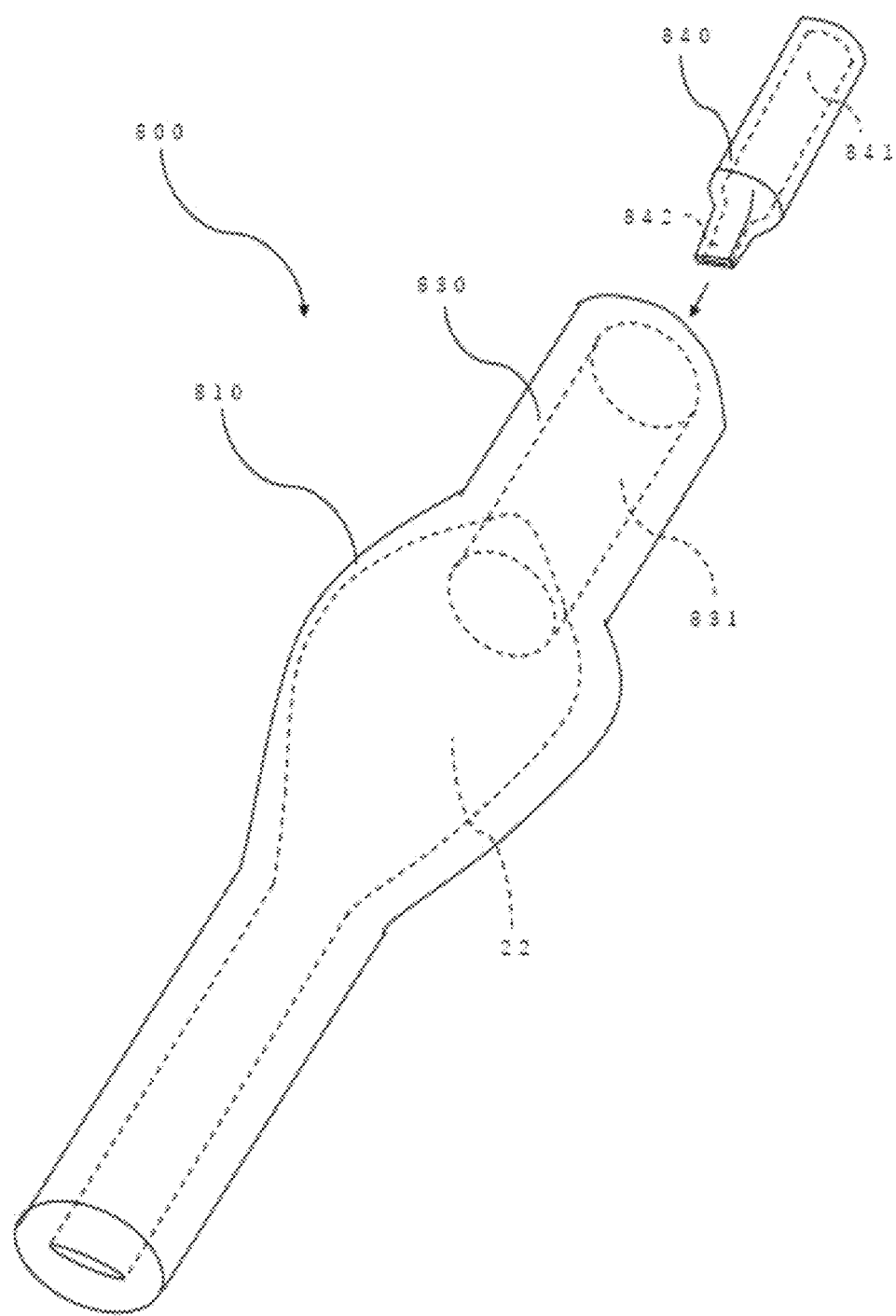
FIG. 23 is a perspective view illustrating a collecting implement according to an eighth embodiment.

FIG. 23 is a perspective view illustrating a collecting implement 800 according to the eighth embodiment.

The collecting implement 800 according to the present embodiment differs from the collecting implement 1 according to the first embodiment in comprising a hollow fitting portion 830 in place of the fitting portion 30 according to the first embodiment. Further, the collecting implement 800 further comprises an inner wear 840.

The hollow fitting portion 830 has a hollow passage 831 which communicates with the collecting portion 22. Further, the inner wear 840 has a tube-shaped fitting portion 841 which fits to and is attached to the genital part of the user and a check valve 842 which is fixed at the head end of the fitting portion 841. The check valve 842 functions similarly to the check valve 40 according to the first embodiment. In the present embodiment, the fitting portion 841 and the check valve 842 are integrally formed in a seamless manner. At least a part of the inner wear 840 (the entirety of the inner wear 840 in the present embodiment) is inserted into the inner side of the hollow fitting portion 830 and the inner wear 840 is combined with the hollow fitting portion 830. In the present embodiment, the inner wear 840 tightly fits to the inner wall of the hollow fitting portion 830. Note that the effects of the present invention are produced when at least a part of the check valve 842 of the inner wear 840 is disposed at any position in the hollow space of a body portion 810. In other words, the check valve 842 may be disposed in the interior of the collecting portion 22.

Ninth Embodiment

Next, a ninth embodiment of the present invention will be described with reference to FIG. 24.

Figure 24:
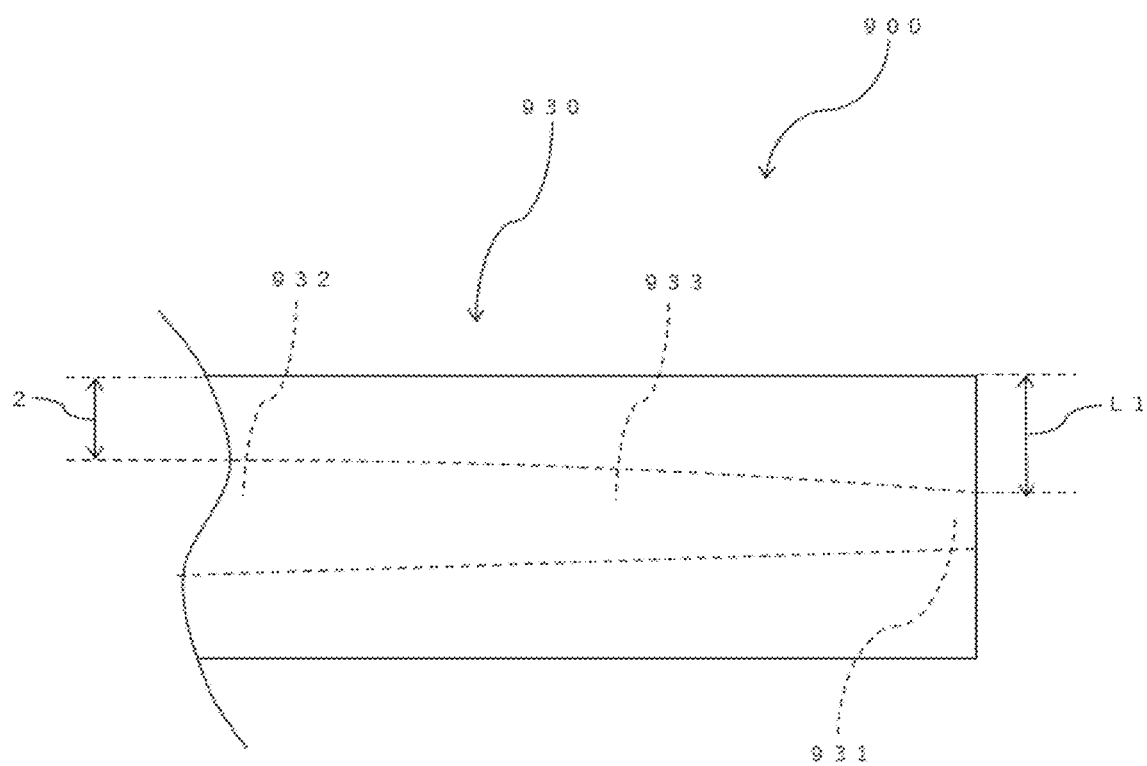
FIG. 24 is a side view illustrating a fitting portion of a collecting implement according to a ninth embodiment.

FIG. 24 is a side view illustrating a fitting portion of a collecting implement according to the ninth embodiment.

A collecting implement 900 according to the present embodiment differs from the collecting implement 1 according to the first embodiment in comprising a fitting portion 930 in place of the fitting portion 30 according to the first embodiment.

The fitting portion 930 has an inlet port 931 and an outlet port 932. The inlet port 931 and the outlet port 932 are connected by means of a communication passage 933. A thickness L1 of the inlet port 931 is provided by a thick part which is thick in the communication passage 933. Meanwhile, a thickness L2 of the outlet port 932 is provided by a thin part which is thin in the communication passage 933. In other words, let the thickness of the thick part be L1 and let the thickness of the thin part be L2, then L1<L2. In the present embodiment, the thickness gradually decreases from the inlet port 931 toward the outlet port 932.

Such an increase of the thickness of the inlet port 931 lowers the stretchability of the thick part. Consequently, the adhesion between the inlet port 931 and a part to be attached is enhanced when the user inserts the part to be attached into the inlet port 931. Thereby, it becomes difficult for the part to be attached to slip out of the fitting portion 930.

Modified Example of Ninth Embodiment

Figure 25:
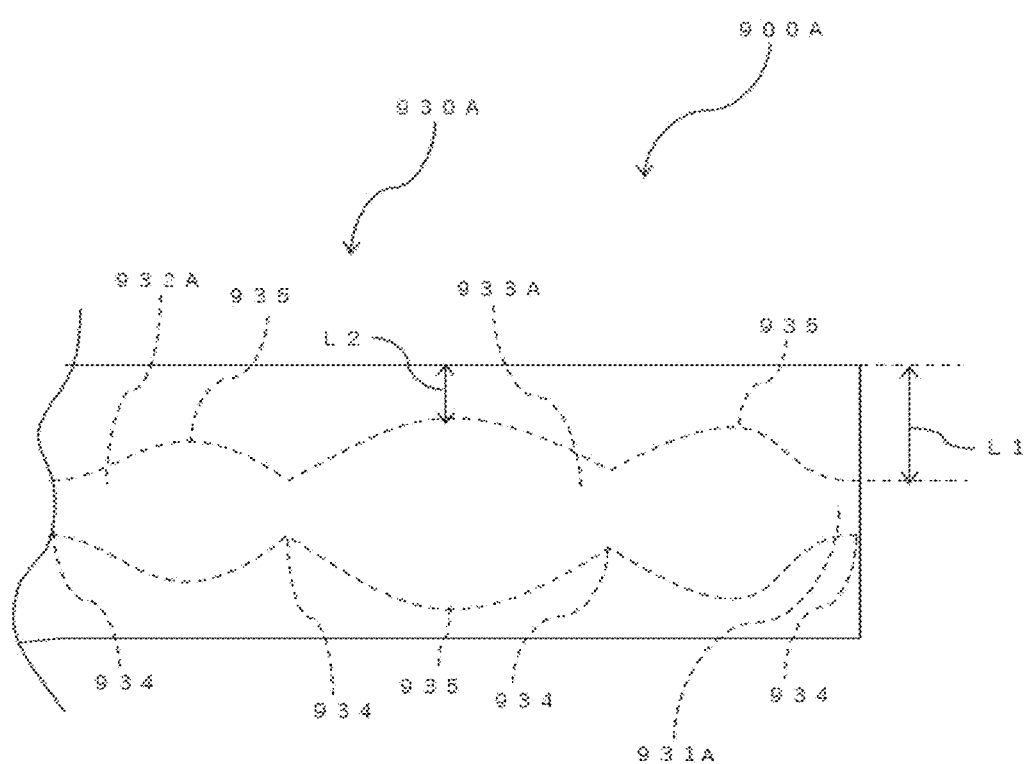
FIG. 25 is a side view illustrating a fitting portion of a collecting implement according to a modified example of the ninth embodiment.

FIG. 25 is a side view illustrating a fitting portion of a collecting implement 900A according to a modified example of the ninth embodiment. A fitting portion 930 according to this modified example has an inlet port 931A and an outlet port 932A. The inlet port 931A and the outlet port 932A are connected by means of a communication passage 933A. In the present embodiment, the communication passage 933A is provided with a plurality of thick parts 934 and a plurality of thin parts 935. The thick parts 934 and the thin parts 935 are alternately arranged. Such a formation of plural parts differing in thickness provides an alternate arrangement of parts having a low stretchability and parts having a high stretchability. In other words, a part to be attached of the user can be provided with parts having a high adhesion and parts having a low adhesion. Consequently, the adhesion between the inlet port 931A and the part to be attached is enhanced when the user inserts the part to be attached into the inlet port 931A. Thereby, it becomes difficult for the part to be attached to slip out of the fitting portion 930A.

Note that as illustrated in FIG. 25, when the outer shape part of the communication passage 933A has a uniform diameter, the communication passage 933A is provided with large diameter parts (thin parts) and small diameter parts (thick parts) in an alternate manner. Then, it is considered that the communication passage 933A produces an effect of a sucker for the part to be attached. Thus, the adhesion between the fitting portion 930A and the part to be attached is enhanced when the user inserts the part to be attached into the fitting portion 930A. Note that although FIG. 25 illustrates the plurality of small diameter parts (thick parts 934) which appear to have substantially the same diameter, the plurality of small diameter parts (thick parts 934) are not limited to having the same diameter. Further, similarly, although it is illustrated that the plurality of large diameter parts (thin parts 935) appear to have substantially the same diameter, the plurality of large diameter parts (thin parts 935) are not limited to having the same diameter. Such an effect of the present embodiment is produced when parts having a relatively small diameter (thick parts) and parts having a relatively large diameter (thin parts) are alternately arranged.

Note that the present invention is not limited to the first embodiment and the second embodiment as described above and variations can be made without departing from the spirit and scope of the present invention.

Figure 26:
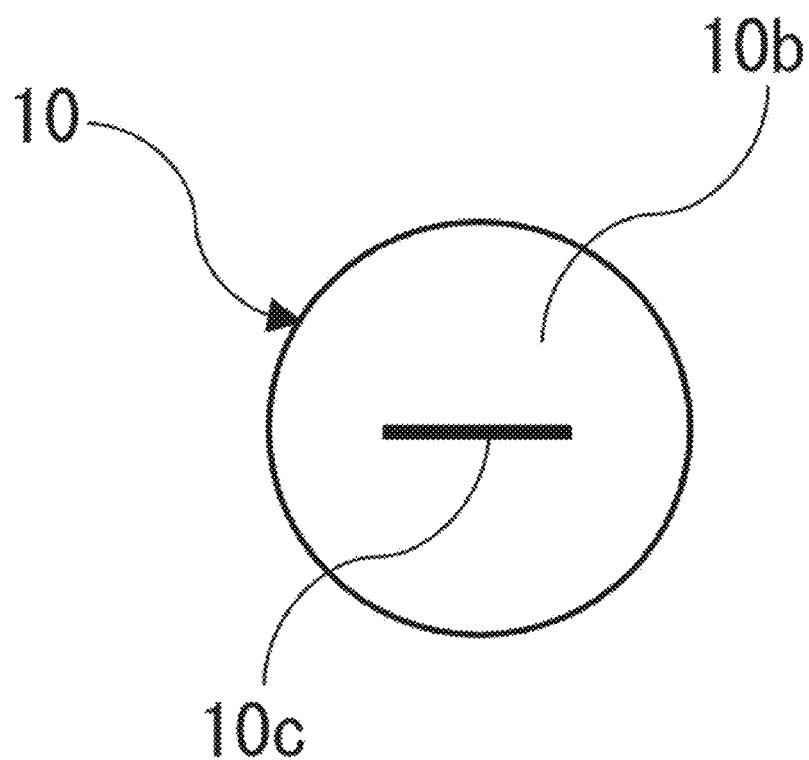
FIG. 26 is a schematic diagram generally illustrating a configuration of an outlet portion of a collecting implement according to another embodiment.

In the first embodiment and the second embodiment as described above, a case in which the outlet portion 23 has a circular opening formed as an outlet port at the other end 10 side of the body portion 10 was explained, but as illustrated in FIG. 26, the opening at the other end 10b side may be formed as a slit 10c.

Thus, the opening at the other end 10b side is formed as the slit 10c so that the outlet port is always closed, thereby preventing the material from unintentionally being discharged from the outlet portion 23. Not only the opening of the outlet portion 23 but also the hollow part (a part or the entirety of the hollow part) may have a slit shape. Also in such a case, the material is prevented from unintentionally being discharged from the outlet portion 23.

In this case, the body portion 10 is bent at the bent portion 11 preferably in a direction vertical to the slit 10c. Thereby, a face in which the slit is cut can be bent. Alternatively, instead of making a cut as a slit, a thinner part than the other part can be formed. Such a thin part produces an effect of easily bending the bent portion 11.

In the above embodiments, a case in which the body portion 10 on the other end 10b side is bent at the bent portion 11 toward the one end 10a side and the outlet portion 23 is thus closed was explained, but it may be configured such that the outlet portion 23 is closed using a member, such as a clip or a rubber band.

In the first embodiment and the second embodiment as described above, a case in which the collecting implement 1(2) is attached to the penis of the user was explained, but the collecting implement may be attached so as to cover the labia of the user, or may be attached so as to cover the anus of the user in view of containing the feces of the user.

In this case, it is needless to say that the fitting portion is configured to have an optional shape to follow the shape of an excretory part and, if necessary, the fitting portion may be supported supplementarily using an underwear or a supporter.

In the first embodiment and the second embodiment as described above, a case in which the body portion 10 has a circular shape was explained, but for the cylindrical shape, various configurations, such as a elliptical cylindrical shape or a polygonal cylindrical shape, can be employed.

In the first embodiment and the second embodiment as described above, a case in which the collecting implement 1(2) is attached to the human body and used for the purpose of collecting the excrement was explained, but for example, the collecting implement 1(2) may be attached to a medical device and used for the purpose of collecting an optional material (for example, blood), may be used for the purpose of collecting the waste liquid from a pipe of a facility, or may be used for the purpose of collecting the sap from a tree.

In such cases, when the collecting implement 1 is attached to an object other than the human body and no material is contained in the collection portion 22, the volume of the collecting implement 1 can be minimized, while an attachment state during attachment of the collecting implement 1 to an object can be flexibly set.

In the above second embodiment, a case in which the body portion 10 and the attachment portion 60 are configured as separate members was explained, but the body portion 10 and the attachment portion 60 may be integrally formed.

Further, in the above embodiments, the predetermined part is thinner than the part other than the predetermined part so as to be more stretchable than the part other than the predetermined part, but is not limited to such a configuration. The predetermined part may be made of a different material than the other part so as to be softer and more stretchable than the part other than the predetermined part. In this case, the predetermined part is joined to the other part by means of adhesion or welding.

REFERENCE SIGNS LIST 1, 2, 100, 400, 500, 600, 700, 800, 900 collecting implement
10 body portion
10a one end
10b the other end
11 bent portion
12 index
20 hollow portion
21 inlet portion
22 (22A) collecting portion
22a (22Aa) bulge portion
23 outlet portion
24 predetermined part
27 support band
28 discharge path
30, 730, 930 fitting portion
40 check valve
50 discharge mechanism
60 attachment portion
61 fitting portion
62 check valve
440 check valve
441 opening part
660 support member
661 body attachment part
662 collecting portion support part
663 outlet portion support part
931 inlet port
932 outlet port
933 communication passage
934 thick part
935 thin part

What is claimed is:

1. A collecting implement comprising: a cylindrical body portion having a softness and a stretchability; and a hollow portion formed in the body portion, wherein
the hollow portion comprises:
an inlet portion which is formed such that one end side of the body portion is open and through which a material is introduced; and
a collecting portion which is formed continuously from the inlet portion, the collecting portion configured to contain the material, and
in the collecting portion, a predetermined part is more stretchable than a part of the collecting portion other than the predetermined part so that the predetermined part can bulge toward an outer side of the body portion when the material introduced from the inlet portion is contained,
wherein the predetermined part is thinner than the part of the collecting portion other than the predetermined portion so as to be more stretchable than the part of the collecting portion other than the predetermined part.

2. The collecting implement according to claim 1, wherein a check valve for preventing the material contained in the collecting portion from flowing back to the inlet portion side is disposed between the collecting portion and the inlet portion.

3. The collecting implement according to claim 1, wherein
the hollow portion comprises:
an outlet portion which is formed to be thick in relation to the collecting portion and communicates with an opening at an opposite end side of the body portion, and through which the material is discharged; and
a discharge mechanism which applies a force acting on the collecting portion in which the material is contained so as to discharge the material through the outlet portion.

4. The collecting implement according to claim 1, wherein a fitting portion which can fit the body portion to an excretory part of the human body is formed integrally with the body portion on the inlet portion side.

5. A collecting implement comprising: a cylindrical body portion having a softness and a stretchability; and a hollow portion formed in the body portion, wherein
the hollow portion comprises:
an inlet portion which is formed such that one end side of the body portion is open and through which a material is introduced; and
a collecting portion which is formed continuously from the inlet portion, the collecting portion configured to contain the material, and
in the collecting portion, a predetermined part is more stretchable than a part of the collecting portion other than the predetermined part so that the predetermined part can bulge toward an outer side of the body portion when the material introduced from the inlet portion is contained,
wherein the predetermined part is made of a different material than the part of the collecting portion other than the predetermined portion so as to be more stretchable than the part of the collecting portion other than the predetermined part.

6. The collecting implement according to claim 5, wherein
a check valve for preventing the material contained in the collecting portion from flowing back to the inlet portion side is disposed between the collecting portion and the inlet portion.

7. The collecting implement according to claim 5, wherein
the hollow portion comprises:
an outlet portion which is formed to be thick in relation to the collecting portion and communicates with an opening at an opposite end side of the body portion, and through which the material is discharged; and a discharge mechanism which applies a force acting on the collecting portion in which the material is contained so as to discharge the material through the outlet portion.

8. The collecting implement according to claim 5, wherein a fitting portion which can fit the body portion to an excretory part of the human body is formed integrally with the body portion on the inlet portion side.

* * * * *